United States Patent
Sohn et al.

(10) Patent No.: US 10,910,088 B2
(45) Date of Patent: Feb. 2, 2021

(54) METHOD AND DEVICE FOR NUCLEIC ACID BASED DIAGNOSTIC APPROACHES INCLUDING THE DETERMINATION OF A DEVIANT CONDITION, ESPECIALLY A HEALTH CONDITION AND/OR A PATHOGENIC CONDITION OF A SAMPLE

(71) Applicants: FRAUNHOFER-GESELLSCHAFT ZUR FÖRDERUNG DER ANGEWANDTEN FORSCHUNG E.V., Munich (DE); UNIVERSITÄT STUTTGART, Stuttgart (DE); MEDIZINISCHE UNIVERSITÄT WIEN, Vienna (AT); UNIVERSITÄT WIEN, Vienna (AT)

(72) Inventors: Kai Sohn, Schwäbisch-Gmünd (DE); Silke Grumaz, Waiblingen (DE); Philip Stevens, Stuttgart (DE); Arndt Von Haeseler, Scharndorf (AT)

(73) Assignees: FRAUNHOFER-GESELLSCHAFT ZUR FÖRDERUNG DER, Munich (DE); UNIVERSITÄT STUTTGART, Stuttgart (DE); MEDIZINISCHE UNIVERSITÄT WIEN, Vienna (AT); UNIVERSITÄT WIEN, Vienna (AT)

( * ) Notice: Subject to any disclaimer, the term of this patent is extended or adjusted under 35 U.S.C. 154(b) by 176 days.

(21) Appl. No.: 15/756,156

(22) PCT Filed: Sep. 8, 2016

(86) PCT No.: PCT/EP2016/071219
§ 371 (c)(1),
(2) Date: Feb. 28, 2018

(87) PCT Pub. No.: WO2017/042287
PCT Pub. Date: Mar. 16, 2017

(65) Prior Publication Data
US 2018/0307795 A1    Oct. 25, 2018

(30) Foreign Application Priority Data

Sep. 10, 2015 (EP) .................................. 15184688

(51) Int. Cl.
*C12Q 1/68* (2018.01)
*G16B 40/00* (2019.01)
(Continued)

(52) U.S. Cl.
CPC .......... *G16B 40/00* (2019.02); *C12Q 1/6869* (2013.01); *G16B 50/00* (2019.02); *C12Q 2535/122* (2013.01); *C12Q 2600/158* (2013.01)

(58) Field of Classification Search
None
See application file for complete search history.

(56) References Cited

U.S. PATENT DOCUMENTS

| 2014/0147851 A1 | 5/2014 | Qian |
| 2016/0253452 A1 | 9/2016 | Karbassi et al. |
| 2016/0289745 A1 | 10/2016 | Labugger et al. |

FOREIGN PATENT DOCUMENTS

| WO | 2012/135815 A2 | 10/2012 |
| WO | 2014/076286 A1 | 5/2014 |

(Continued)

OTHER PUBLICATIONS

1) Cheng Weixiao et al: "Abundance and persistence of antibiotic resistance genes in livestock farms: A comprehensive investigation in eastern China", Environment International, vol. 61, Oct. 2, 2013, pp. 1-7, XP028761720.
(Continued)

*Primary Examiner* — Aaron A Priest
(74) *Attorney, Agent, or Firm* — Pearne & Gordon LLP

(57) ABSTRACT

The present invention relates to a method and a device for a nucleic acid based diagnostic approach including the
(Continued)

Figure 1:
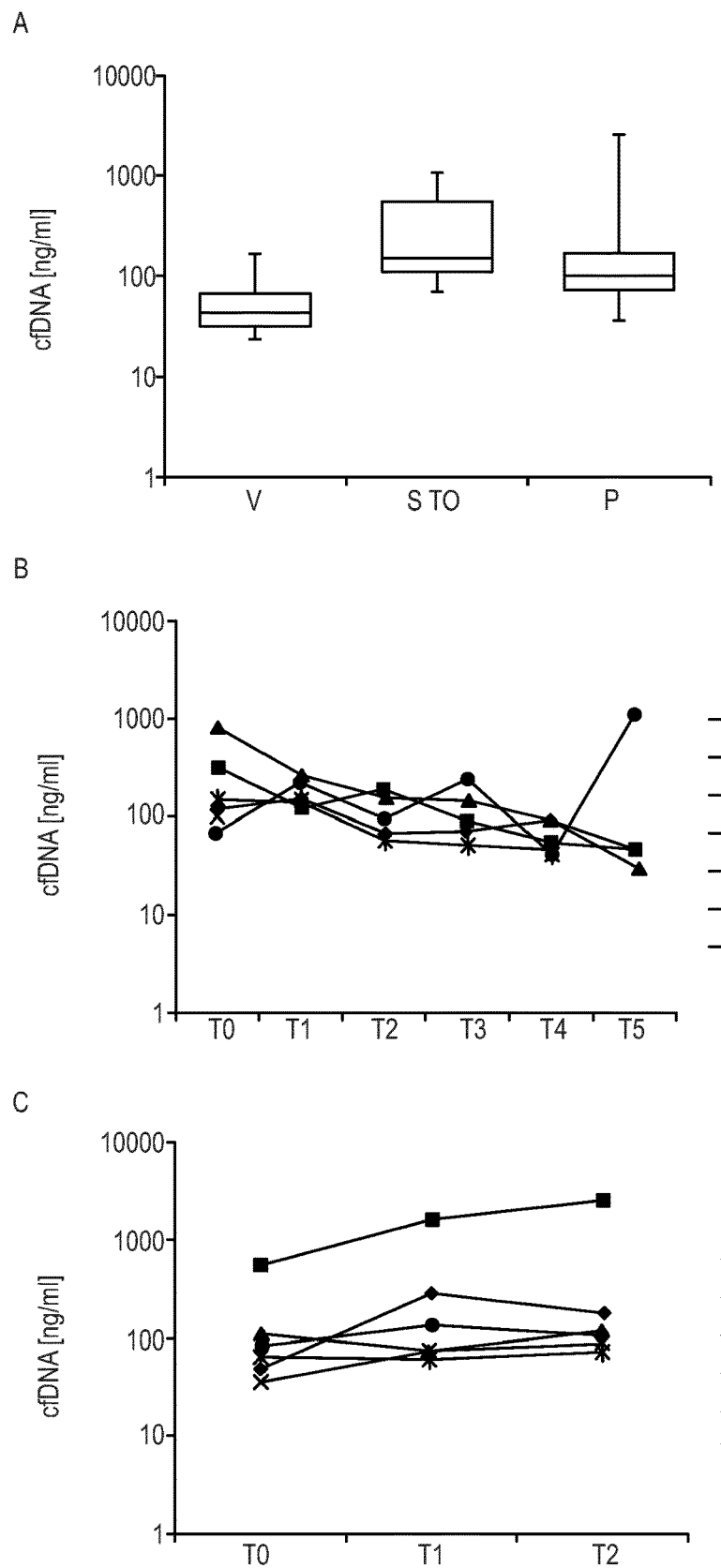

determination of a deviant condition of a sample, wherein the deviant condition is preferably a health condition and/or a pathogenic condition.

14 Claims, 31 Drawing Sheets

Specification includes a Sequence Listing.

(51) Int. Cl.
*G16B 50/00* (2019.01)
*C12Q 1/6869* (2018.01)

(56) References Cited

FOREIGN PATENT DOCUMENTS

| WO | WO-2014076286 A1 * | 5/2014 | ............ C12Q 1/689 |
| WO | 2014145232 A2 | 9/2014 | |
| WO | 2015/061422 A1 | 4/2015 | |
| WO | WO-2015061422 A1 * | 4/2015 | ............ G16B 20/00 |
| WO | 2015/070086 A1 | 5/2015 | |

OTHER PUBLICATIONS

2) Mardis Elaine R:, "Next-generation DNA sequencing methods", Annual Review of Genomics and Human Genetics, Annual Reviews, US, vol. 9, Jun. 24, 2008, pp. 387-402, XP002512993.
3) Silke Grumaz et al: "Next-generation sequencing diagnostics of bacteremia in septic patients", Genome Medicine, vol. 19, No. 6, Jul. 1, 2016, p. 513, XP055327289.
International Search Report dated Dec. 19, 2016 for corresponding International Application No. PCT/EP2016/071219.
Written Opinion dated Dec. 19, 2016 for corresponding International Application No. PCT/EP2016/071219.
Notice of Reasons for Rejection dated Jun. 30, 2020 for corresponding Japanese Application No. 2018-513557 and English translation.
Schmieder et al., "Insights into antibiotic resistance through metagenomic approaches", Future Microbiol, 2012, 7(1), pp. 73-89, ISSN 1746-0913.

* cited by examiner

E

Fig. 4

B

| CARD ID | Alias | Gene coverage | Read Count | Source |
|---|---|---|---|---|
| JQ727667.1.gene1 | robA | 0.58 | 5 | [E. cloacae] |
| CP001918.1.gene250 | rpoB | 0.25 | 11 | [E. cloacae subsp. cloacae ATCC 13047] |
| CP001138.1.gene4362 | rpoB | 0.05 | 1 | [S. enterica subsp. enterica serovar Agona str. SL483] |
| FN543093.2.gene314 | rpoB | 0.02 | 1 | [C. turicensis z3032] |
| CP000034.1.gene3741 | rpoB | 0.02 | 1 | [S. dysenteriae Sd197] |

C

```
mecA    AATAAATTAACCGAAGATAAAAAGAACCTCTGCTCAACAAGTTCCAGATTACAACTTCA
SX2_r1  ------------------------------------------CAGATTACAACTTCA
SX2_r2  ------------------------------------------CAGATTACAACTTCA
SX2_r3  ---------------------------------------------ATTACAACTTCA
                                                   ************ mecA    CCAGGTTCAACTCAAAAAATATTAACAGCAATGATTGGGTTAAATAACAAAACATTAGAC
SX2_r1  CCAGGTTCAACTCAAAAAATATTAACAGCAATGATTGGGTTAAATAACAAAACATTAGAC
SX2_r2  CCAGGTTCAACTCAAAAAATATTAACAGCAATGATTGGGTTAAATAACAAAACATTAGAC
SX2_r3  CCAGGTTCAACTCAAAAAATATTAACAGCAATGATTGGGTTAAATAACAAAACATTAGAC
        ************************************************************ mecA    GATAAAACAAGTTATAAAATCGATGGTAAAGGTTGGCAAAAAGATAAATCTTGGGGTGGT
SX2_r1  GATAAAACAAGTTATAAAATCGATGGTAAAGGTTGGCAAAAAGATAAATCTTGGGGTGGT
SX2_r2  GATAAAACAAGTTATAAAATCGATGGTAAAGGTTGGCAAAAAGATAAATCTTGGGGTGGT
SX2_r3  GATAAAACAAGTTATAAAATCGATGGTAAAGGTTGGCAAAAAGATAAATCTTGGGGTGGT
        ************************************************************ mecA    TACAACGTTACAAGATATGAAGTGGTAAATGGTAATATCGACTTAAAACAAGCAATAGAA
SX2_r1  TACAACGTTACAAGA---------------------------------------------
SX2_r2  TACAACGTTACAAGA---------------------------------------------
SX2_r3  TACAACGTTACAAGA---------------------------------------------
        ***************
```

B III

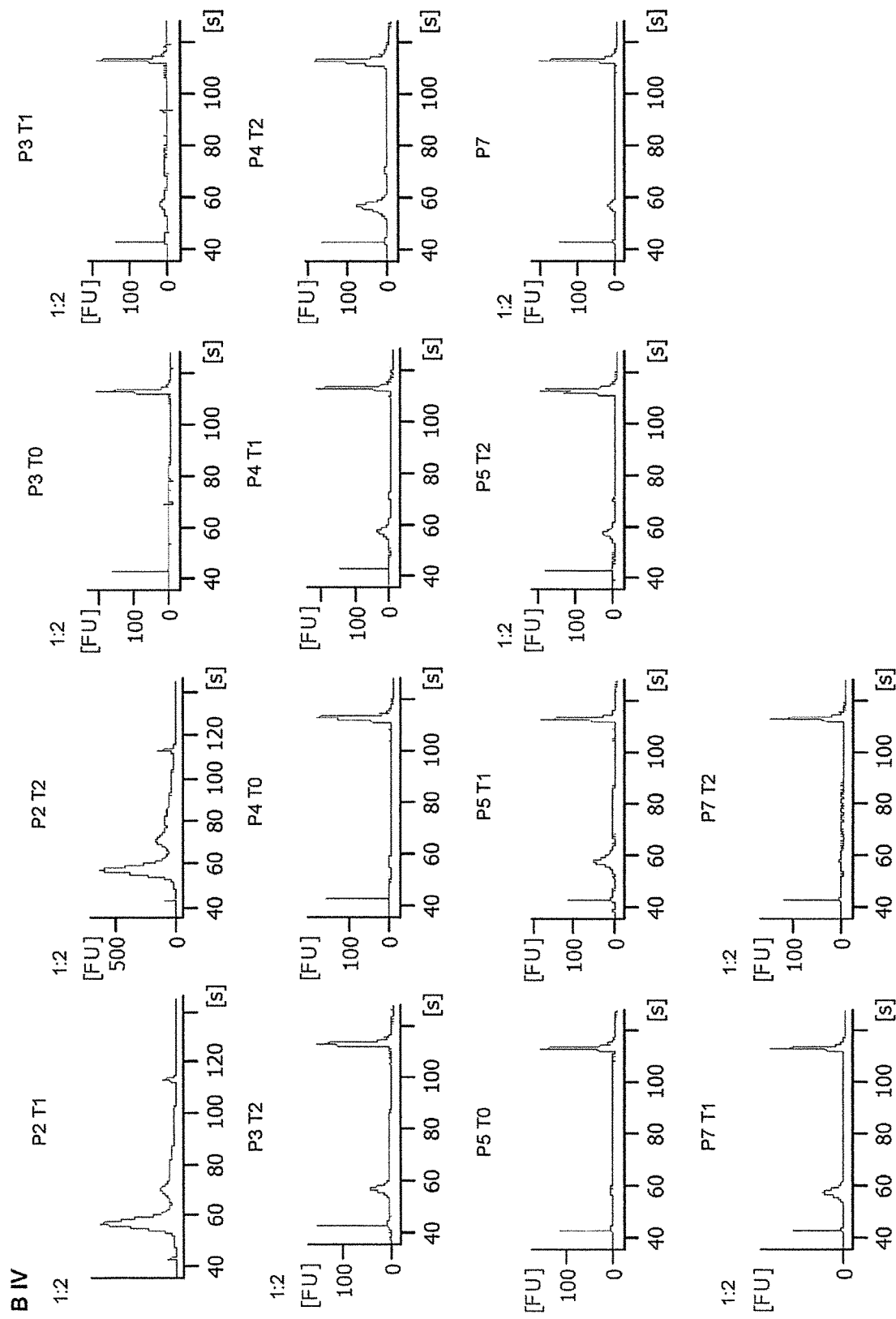

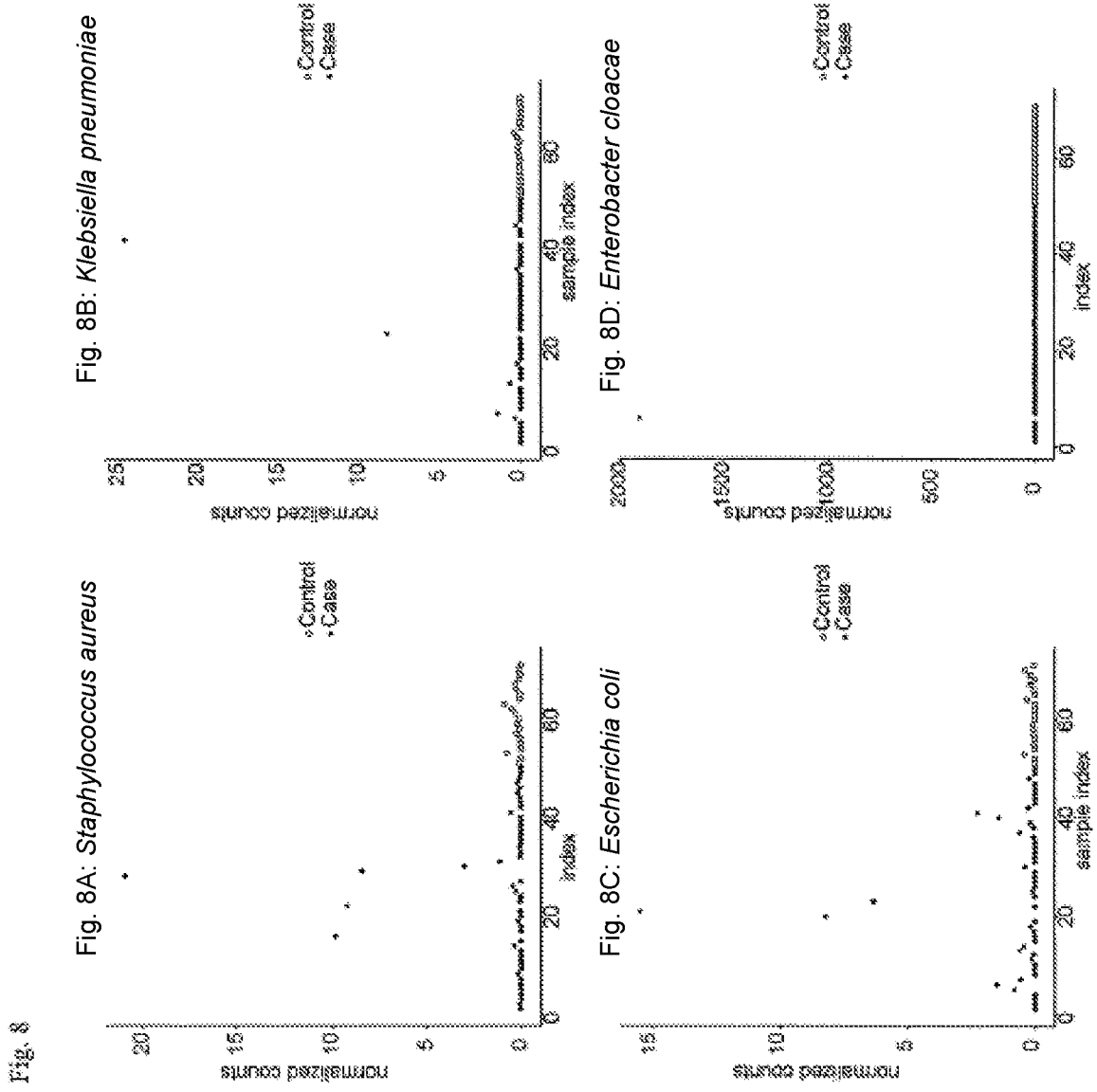

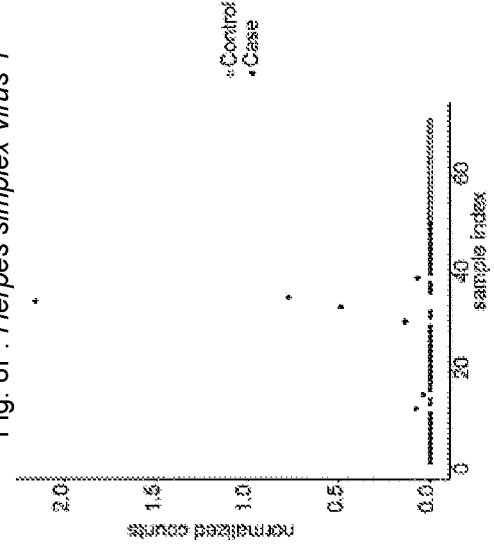
Fig. 8F: Herpes simplex virus 1
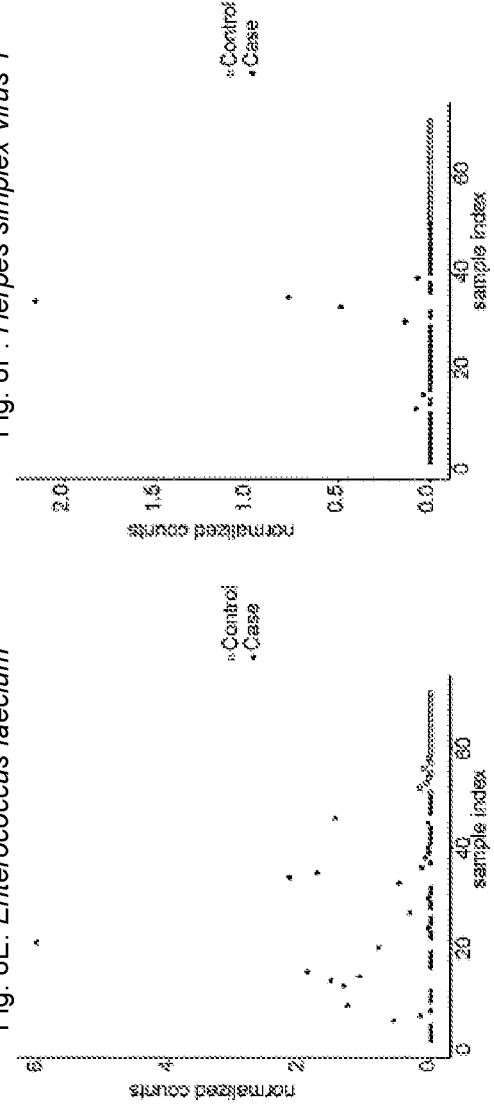
Fig. 8E: Enterococcus faecium

Fig. 14

| ID | Time | Sex | Age | cfDNA [ng/ml plasma] | Sequencing depth | Human reads | Un-mapped | Classified |
|---|---|---|---|---|---|---|---|---|
| S9 | T0 | m | 82 | 120.59 | 30,650,143 | 92.90% | 7.10% | 28.90% |
| S10 | T0 | m | 68 | 307.83 | 27,199,593 | 98.70% | 1.30% | 2.85% |
| S11 | T0 | m | 62 | 805.50 | 27,073,879 | 93.61% | 6.39% | 20.73% |
| S19 | T0 | f | 62 | 101.30 | 26,892,684 | 98.45% | 1.55% | 4.75% |
| S23 | T0 | m | 79 | 146.70 | 24,917,032 | 97.12% | 2.88% | 3.85% |
| S26 | T0 | m | 66 | 1088.90 | 32,529,889 | 96.60% | 3.40% | 3.24% |
| S60 | T0 | f | 70 | 70.29 | 27,381,853 | 97.10% | 2.90% | 4.40% |
| | average S T0 | | 70 | 377.30 | 28,092,153 | 96.36% | 3.64% | 9.82% |
| | average S all | | 70 | 197.23 | 25,960,730 | 97.79% | 2.21% | 4.24% |
| V5 | | m | 24 | 35.80 | 34,203,815 | 81.90% | 18.10% | 12.38% |
| V6 | | m | 29 | 27.40 | 30,000,000 | 98.96% | 1.04% | 2.25% |
| V7 | | f | 22 | 76.40 | 21,004,601 | 96.58% | 3.42% | 2.35% |
| V13 | | f | 26 | 23.50 | 24,449,232 | 98.09% | 1.91% | 3.26% |
| V14 | | m | 28 | 38.60 | 37,971,559 | 97.42% | 2.58% | 1.79% |
| V15 | | m | 27 | 166.80 | 24,505,696 | 97.60% | 2.40% | 2.88% |
| V16 | | f | 29 | 70.60 | 27,220,925 | 97.06% | 2.94% | 2.67% |
| V17 | | m | 26 | 28.40 | 20,225,374 | 98.61% | 1.39% | 3.30% |
| V18 | | m | 28 | 48.80 | 19,157,938 | 98.14% | 1.86% | 2.46% |
| V19 | | f | 31 | 33.40 | 25,776,920 | 97.08% | 2.92% | 2.87% |
| V21 | | m | 22 | 67.30 | 25,220,391 | 97.72% | 2.28% | 2.51% |
| V22 | | m | 25 | 48.20 | 30,000,000 | 99.15% | 0.85% | 3.25% |
| | average V | | 26 | 55.43 | 26,644,704 | 96.52% | 3.48% | 3.50% |
| P1 | T0 | m | 58 | 50.20 | 22,389,868 | 96.95% | 3.05% | 1.79% |
| P2 | T0 | m | 53 | 552.00 | 30,000,000 | 98.57% | 1.43% | 3.35% |
| P3 | T0 | f | 62 | 109.50 | 18,796,573 | 94.69% | 5.31% | 1.38% |
| P4 | T0 | f | 72 | 36.42 | 28,457,744 | 94.91% | 5.09% | 4.59% |
| P5 | T0 | m | 64 | 65.38 | 28,547,804 | 95.48% | 4.52% | 3.72% |
| P7 | T0 | m | 76 | 82.50 | 28,845,398 | 96.69% | 3.31% | 1.00% |
| | average P T0 | | 64 | 149.33 | 26,172,898 | 96.21% | 3.79% | 2.64% |
| | average P T1-T2 | | 64 | 451.63 | 25,406,269 | 97.72% | 2.28% | 2.14% |
| | average P all | | 64 | 350.86 | 25,661,812 | 97.22% | 2.78% | 2.31% |

Fig. 15

| Organism | NCBI taxonomy ID |
|---|---|
| Aspergillus fumigatus | 330879 |
| Aspergillus nidulans | 227321 |
| Aspergillus niger | 425011 |
| Aspergillus oryzae | 510516 |
| Candida albicans | 1182532 |
| Candida albicans | 237561 |
| Candida albicans | 294748 |
| Candida dubliniensis | 573826 |
| Candida glabrata | 284593 |
| Candida parapsilosis | 578454 |
| Candida tropicalis | 294747 |
| Cryptococcus gattii | 367775 |

Fig. 16A

| ID | Time | Sex | Age | cfDNA [ng/ml plasma] | Sequencing depth | Human reads [%] | Unmapped [%] | Classified [%] | E. coli | | E. cloacae | | E. faecium | | K. pneumoniae | | S. aureus | |
|---|---|---|---|---|---|---|---|---|---|---|---|---|---|---|---|---|---|---|
| | | | | | | | | | Scaled reads | SIQ score | Scaled reads | SIQ score | Scaled reads | SIQ score | Scaled reads | SIQ score | Scaled reads | SIQ score |
| S9 | T0 | m | 82 | 120.6 | 30,650,143 | 92.90 | 7.10 | 28.90 | 1.5 | 3.8 | 1907.3 | 586795.1 | 0.2 | 0.3 | 0.4 | 0.4 | 0.0 | 0.0 |
| S9 | T1 | m | 82 | 155.9 | 23,756,911 | 98.86 | 1.14 | 2.08 | 0.0 | 0.0 | 0.3 | 0.2 | 0.0 | 0.1 | 0.0 | 0.0 | 0.0 | 0.0 |
| S9 | T2 | m | 82 | 69.2 | 26,075,281 | 98.71 | 1.29 | 4.16 | 0.1 | 0.1 | 0.3 | 0.2 | 0.0 | 0.0 | 0.0 | 0.0 | 0.3 | 0.2 |
| S9 | T3 | m | 82 | 72.0 | 32,978,324 | 98.63 | 1.37 | 6.31 | 0.0 | 0.0 | 4.7 | 24.2 | 0.0 | 0.0 | 0.0 | 0.1 | 0.5 | 0.3 |
| S9 | T4 | m | 82 | 91.2 | 28,294,395 | 98.66 | 1.34 | 1.88 | 0.0 | 0.0 | 0.6 | 0.0 | 0.3 | 0.6 | 0.0 | 0.0 | 0.0 | 0.0 |
| S9 | T5 | m | 82 | 48.1 | 4,595,909 | 98.98 | 3.02 | 5.03 | 0.0 | 0.0 | 0.0 | 0.4 | 1.3 | 4.8 | 0.0 | 0.0 | 0.2 | 0.1 |
| S10 | T0 | m | 68 | 307.8 | 28,199,593 | 98.70 | 1.30 | 2.85 | 0.0 | 0.0 | 0.2 | 0.1 | 0.0 | 0.0 | 0.0 | 0.0 | 9.2 | 125.2 |
| S10 | T1 | m | 68 | 121.9 | 24,833,414 | 98.62 | 1.38 | 3.73 | 0.0 | 0.0 | 0.0 | 0.0 | 0.0 | 0.0 | 0.0 | 0.0 | 20.9 | 720.4 |
| S10 | T2 | m | 68 | 191.7 | 16,121,548 | 98.72 | 1.28 | 2.52 | 0.0 | 0.0 | 0.0 | 0.0 | 0.0 | 0.0 | 0.0 | 0.0 | 8.4 | 100.7 |
| S10 | T3 | m | 68 | 90.0 | 27,764,474 | 98.65 | 1.35 | 1.71 | 0.4 | 0.4 | 0.0 | 0.0 | 0.0 | 0.1 | 0.0 | 0.0 | 3.0 | 12.9 |
| S10 | T4 | m | 68 | 55.4 | 13,108,733 | 98.49 | 1.51 | 1.35 | 0.0 | 0.0 | 0.0 | 0.0 | 0.0 | 0.0 | 0.0 | 0.0 | 1.1 | 2.0 |
| S10 | T5 | m | 68 | 47.1 | 24,045,568 | 98.19 | 1.81 | 1.34 | 0.0 | 0.0 | 0.0 | 0.0 | 0.0 | 0.0 | 0.0 | 0.0 | 0.0 | 0.0 |

Fig. 16B

| Sample | T | Sex | Age | Weight | Count | % | V1 | V2 | V3 | V4 | V5 | V6 | V7 | V8 | V9 | V10 | V11 | V12 |
|---|---|---|---|---|---|---|---|---|---|---|---|---|---|---|---|---|---|---|
| S1_1 | T0 | m | 62 | 805.5 | 27,073,879 | 93.61 | 6.39 | 20.73 | 0.6 | 0.6 | 0.1 | 0.1 | 0.0 | 0.0 | 1.5 | 3.9 | 0.0 | 0.0 |
| S1_1 | T1 | m | 62 | 258.5 | 28,978,582 | 96.57 | 3.43 | 4.36 | 0.0 | 0.0 | 0.0 | 0.0 | 0.0 | 0.0 | 0.0 | 0.0 | 0.0 | 0.0 |
| S1_1 | T2 | m | 62 | 156.9 | 30,279,377 | 96.75 | 3.25 | 2.15 | 0.1 | 0.0 | 0.1 | 0.0 | 0.0 | 0.0 | 0.0 | 0.0 | 0.0 | 0.0 |
| S1_1 | T3 | m | 62 | 146.8 | 34,056,623 | 96.61 | 3.39 | 2.88 | 0.0 | 0.0 | 0.0 | 0.1 | 0.0 | 0.0 | 0.0 | 0.0 | 0.0 | 0.0 |
| S1_1 | T4 | m | 62 | 92.0 | 28,324,033 | 98.83 | 3.17 | 2.75 | 0.8 | 0.1 | 0.0 | 0.0 | 1.3 | 5.0 | 0.0 | 0.8 | 0.0 | 0.0 |
| S1_1 | T5 | m | 62 | 31.2 | 24,184,187 | 98.85 | 3.15 | 2.67 | 6.4 | 0.6 | 0.8 | 0.0 | 1.5 | 5.7 | 0.7 | 0.1 | 0.0 | 0.0 |
| S1_1 | T6 | m | 62 | 101.3 | 26,892,684 | 98.45 | 1.55 | 4.75 | 0.0 | 72.2 | 0.0 | 0.1 | 0.0 | 0.0 | 8.4 | 0.0 | 0.0 | 0.0 |
| S2_3 | T0 | f | 79 | 148.7 | 24,917,032 | 97.12 | 2.88 | 3.85 | 0.0 | 0.0 | 0.1 | 0.1 | 1.9 | 7.1 | 0.0 | 0.0 | 0.0 | 0.0 |
| S2_3 | T1 | m | 79 | 148.2 | 10,254,988 | 98.79 | 1.21 | 2.33 | 0.0 | 0.0 | 0.1 | 0.0 | 0.5 | 0.8 | 0.0 | 0.0 | 0.0 | 0.0 |
| S2_3 | T2 | m | 79 | 57.6 | 34,802,147 | 98.77 | 1.23 | 1.85 | 0.0 | 0.0 | 0.0 | 0.0 | 2.2 | 12.8 | 0.0 | 0.0 | 0.0 | 0.0 |
| S2_3 | T3 | m | 79 | 52.8 | 29,368,101 | 98.73 | 1.27 | 2.39 | 0.0 | 0.0 | 0.0 | 0.1 | 1.7 | 6.5 | 0.0 | 0.0 | 0.0 | 0.0 |
| S2_3 | T4 | m | 79 | 48.2 | 27,815,028 | 98.64 | 1.36 | 2.11 | 0.0 | 0.0 | 0.0 | 0.0 | 0.1 | 0.2 | 0.0 | 0.3 | 0.0 | 0.0 |
| S2_6 | T0 | m | 66 | 1088.9 | 32,529,889 | 98.60 | 3.40 | 3.24 | 15.5 | 476.5 | 0.0 | 0.0 | 8.0 | 96.0 | 0.0 | 0.0 | 0.0 | 134.1 |
| S6_o | T0 | f | 70 | 70.3 | 27,381,853 | 97.10 | 2.90 | 4.40 | 0.6 | 0.6 | 0.0 | 0.0 | 0.0 | 0.0 | 0.0 | 0.0 | 9.8 | 0.0 |
| S6_o | T1 | f | 70 | 220.3 | 29,925,196 | 98.50 | 1.50 | 2.12 | 0.0 | 0.6 | 0.0 | 0.0 | 0.2 | 0.0 | 0.0 | 0.0 | 0.0 | 0.0 |
| S6_o | T2 | f | 70 | 95.2 | 33,149,906 | 98.59 | 1.41 | 2.94 | 0.2 | 0.0 | 0.0 | 0.0 | 0.1 | 0.2 | 0.0 | 0.0 | 0.0 | 0.0 |
| S6_o | T3 | f | 70 | 242.6 | 28,611,714 | 98.62 | 1.38 | 1.95 | 0.2 | 0.2 | 0.0 | 0.0 | 0.0 | 0.1 | 0.0 | 0.0 | 0.0 | 0.0 |

Fig. 16C

| | T4 | | | | | | | | | | | | | | | | | |
|---|---|---|---|---|---|---|---|---|---|---|---|---|---|---|---|---|---|---|
| S60 | f | 70 | 42.9 | 25,200,511 | 98.73 | 1.27 | 2.01 | 1.4 | 3.6 | 0.0 | 0.0 | 0.0 | 0.1 | 0.0 | 0.0 | 0.0 | 0.0 | 0.0 |
| S80 | f | 70 | 60.7 | 27,734,315 | 98.58 | 1.42 | 2.06 | 2.3 | 9.2 | 0.0 | 0.0 | 0.0 | 0.0 | 0.0 | 0.0 | 0.0 | 0.5 | 0.4 |
| S80 | f | 70 | 1080.0 | 22,039,017 | 98.61 | 1.39 | 2.44 | 0.3 | 0.3 | 0.1 | 0.1 | 0.0 | 0.0 | 24.7 | 1341.4 | 0.0 | 0.0 | 0.0 |
| S80 | | | | | | | | | | | | 0.0 | | | | 0.8 | |
| G5 | m | 24 | 35.8 | 34,203,815 | 81.80 | 18.10 | 12.38 | 0.4 | 0.3 | 0.3 | 0.0 | 0.1 | 0.0 | | | | | |
| G6 | m | 29 | 27.4 | 30,000,000 | 98.96 | 1.04 | 2.25 | 0.0 | 0.0 | 0.0 | 0.1 | 0.0 | 0.0 | | | 0.0 | | |
| G7 | f | 22 | 76.4 | 21,004,601 | 96.58 | 3.42 | 2.35 | 0.0 | 0.0 | 0.4 | 0.0 | 0.0 | 0.1 | | | | 0.1 | |
| G13 | f | 26 | 23.5 | 24,449,232 | 98.09 | 1.91 | 3.26 | 0.1 | 0.1 | 0.3 | 0.1 | 0.0 | 0.1 | | | | 0.3 | |
| G14 | m | 28 | 38.6 | 37,971,559 | 97.42 | 2.58 | 1.79 | 0.1 | 0.1 | 0.5 | 0.0 | 0.0 | 0.0 | | | | 0.1 | |
| G15 | m | 27 | 166.8 | 24,505,696 | 97.60 | 2.40 | 2.88 | 0.1 | 0.1 | 0.2 | 0.1 | 0.0 | 0.1 | | | | 0.2 | |
| G16 | f | 29 | 70.6 | 27,220,925 | 87.06 | 2.94 | 2.67 | 0.0 | 0.0 | 0.4 | 0.2 | 0.0 | 0.2 | | | | 0.1 | |
| G17 | m | 28 | 28.4 | 20,225,374 | 98.61 | 1.39 | 3.30 | 0.0 | 0.0 | 0.2 | 0.2 | 0.0 | 0.2 | | | | 0.3 | |
| G18 | m | 28 | 48.8 | 19,157,938 | 98.14 | 1.86 | 2.48 | 0.0 | 0.0 | 2.1 | 0.1 | 0.0 | 0.1 | | | | 0.5 | |
| G19 | f | 31 | 33.4 | 25,776,920 | 97.08 | 2.92 | 2.87 | 0.0 | 0.0 | 0.1 | 0.1 | 0.0 | 0.2 | | | | 0.9 | |
| C21 | m | 22 | 67.3 | 25,220,391 | 97.72 | 2.28 | 2.51 | 0.3 | 0.3 | 0.1 | 0.2 | 0.0 | 0.4 | | | | 0.1 | |
| G22 | m | 25 | 48.2 | 30,000,000 | 99.15 | 0.85 | 3.25 | 0.0 | 0.0 | 0.5 | 0.0 | 0.0 | 0.0 | | | | 0.0 | |
| P1-T0 | m | 58 | 50.2 | 22,388,868 | 96.95 | 3.05 | 1.79 | 0.0 | 0.0 | 0.0 | 0.0 | 0.0 | 0.0 | | | 0.0 | 0.1 | 0.0 |
| P1-T1 | m | 58 | 281.6 | 22,030,372 | 98.19 | 1.81 | 2.77 | 0.0 | 0.0 | 0.0 | 0.0 | 0.0 | 0.0 | | | 0.0 | 0.1 | 0.0 |

Fig. 16D

| | | | | | | | | | | | | | | | | | |
|---|---|---|---|---|---|---|---|---|---|---|---|---|---|---|---|---|---|
| P1 | T2 | m | 58 | 180.0 | 26,793,386 | 98.21 | 1.79 | 3.80 | 0.0 | 0.0 | 0.0 | 0.0 | 0.0 | 0.0 | 0.0 | 0.1 | 0.1 |
| P2 | T0 | m | 53 | 552.0 | 30,000,000 | 98.57 | 1.43 | 3.35 | 0.0 | 0.0 | 0.2 | | 0.0 | 0.0 | | 3.0 | |
| P2 | T1 | m | 53 | 1645.9 | 25,792,012 | 98.48 | 1.52 | 2.06 | 0.0 | 0.0 | 0.0 | 0.0 | 0.0 | 0.0 | 0.0 | 0.0 | 0.0 |
| P2 | T2 | m | 53 | 2573.3 | 28,208,869 | 98.64 | 1.36 | 2.05 | 0.0 | 0.0 | 0.0 | 0.0 | 0.0 | 0.0 | 0.0 | 0.0 | 0.0 |
| P3 | T0 | f | 62 | 108.5 | 18,796,573 | 94.69 | 5.31 | 1.38 | 0.0 | 0.0 | 0.0 | 0.0 | 0.0 | 0.0 | | 0.1 | |
| P3 | T1 | f | 62 | 77.0 | 22,019,102 | 97.41 | 2.59 | 1.20 | 0.0 | 0.1 | 0.0 | 0.0 | 0.0 | 0.0 | 0.0 | 0.0 | 0.0 |
| P3 | T2 | f | 62 | 118.6 | 30,293,787 | 97.61 | 2.39 | 1.35 | 0.0 | 0.0 | 0.2 | 0.0 | 0.0 | 0.0 | 0.0 | 0.0 | 0.0 |
| P4 | T0 | f | 72 | 36.4 | 28,457,744 | 94.91 | 5.09 | 4.69 | 0.2 | 0.0 | 0.0 | 0.1 | 0.1 | 0.0 | 0.4 | 0.3 | 0.1 |
| P4 | T1 | f | 72 | 72.0 | 23,764,397 | 97.55 | 2.45 | 2.47 | 0.0 | 0.0 | 0.0 | 0.3 | 5.5 | 0.3 | 0.0 | 0.2 | 0.0 |
| P4 | T2 | f | 72 | 90.0 | 25,359,109 | 97.83 | 2.17 | 1.91 | 0.0 | 0.0 | 0.0 | 0.0 | 0.0 | 0.0 | 0.0 | 0.0 | 0.0 |
| P5 | T0 | m | 84 | 65.4 | 28,547,804 | 96.48 | 4.52 | 3.72 | 0.2 | 0.0 | 0.0 | 0.0 | 0.0 | 0.0 | 0.0 | 0.3 | 0.1 |
| P5 | T1 | m | 84 | 63.5 | 17,572,786 | 97.30 | 2.70 | 2.22 | 0.0 | 0.2 | 0.0 | 0.1 | 0.0 | 0.0 | 0.0 | 0.2 | 0.1 |
| P5 | T2 | m | 84 | 75.8 | 32,670,764 | 97.10 | 2.90 | 2.92 | 0.2 | 0.0 | 0.0 | 0.1 | 0.0 | 0.0 | 0.0 | 0.1 | 0.1 |
| P7 | T0 | m | 76 | 82.5 | 28,845,398 | 98.69 | 3.31 | 1.00 | 0.0 | 0.0 | 0.0 | | 0.0 | 0.0 | | 0.1 | 0.1 |
| P7 | T1 | m | 76 | 135.6 | 23,618,572 | 97.90 | 2.10 | 1.79 | 0.0 | 0.0 | 0.0 | 0.0 | 0.0 | 0.0 | 0.0 | 0.0 | 0.0 |
| P7 | T2 | m | 76 | 106.4 | 24,696,097 | 96.39 | 3.61 | 1.33 | 0.0 | 0.0 | 0.0 | 0.0 | 0.0 | 0.0 | 0.0 | 0.0 | 0.0 |

Fig. 17

Name

| | |
|---|---|
| *Acidovorax ebreus* | *Paramecium bursaria Chlorella virus A1* |
| *Akkermansia muciniphila* | *Polynucleobacter necessarius* |
| *Anaerococcus prevotii* | *Porphyromonas gingivalis* |
| *Bacillus coagulans* | *Pseudomonas poae* |
| *Bacillus megaterium* | *Pseudomonas protegens* |
| *Bacteroides vulgatus* | *Pseudomonas sp. VLB120* |
| *Bifidobacterium longum* | *Psychrobacter sp. PRwf-1* |
| *Bifidobacterium thermophilum* | *Rhizobium sp. IRBG74* |
| *Bradyrhizobium sp. BTAi1* | *Ruminococcus bromii* |
| *Burkholderia lata* | *Salmonella enterica* |
| *Burkholderia sp. YI23* | *Sphingomonas sp. MM-1* |
| *Burkholderia vietnamiensis* | *Staphylococcus pasteuri* |
| *Burkholderia xenovorans* | *Staphylococcus phage StB20* |
| *butyrate-producing bacterium SSC/2* | *Staphylococcus saprophyticus* |
| *Citrobacter koseri* | *Streptococcus gordonii* |
| *Collimonas fungivorans* | *Streptococcus pseudopneumoniae* |
| *Corynebacterium diphtheriae* | *Streptococcus sp. I-G2* |
| *Corynebacterium kroppenstedtii* | *Streptococcus sp. I-P16* |
| *Corynebacterium urealyticum* | *Thermobispora bispora* |
| *Corynebacterium variabile* | *Thermus scotoductus* |
| *Cupriavidus necator* | *Xanthobacter autotrophicus* |
| *Debaryomyces hansenii* | |
| *Enterobacteria phage M13* | |
| *Escherichia coli* | |
| *Eubacterium rectale* | |
| *Faecalibacterium prausnitzii* | |
| *Flavobacterium branchiophilum* | |
| *Human herpesvirus 6B* | |
| *Lactobacillus buchneri* | |
| *Lactobacillus delbrueckii* | |
| *Lactobacillus gasseri* | |
| *Lactobacillus helveticus* | |
| *Lactobacillus johnsonii* | |
| *Lactobacillus plantarum* | |
| *Lactobacillus ruminis* | |
| *Legionella pneumophila* | |
| *Meiothermus ruber* | |
| *Methylobacterium populi* | |
| *Methylobacterium radiotolerans* | |
| *Neisseria meningitidis* | |
| *Parabacteroides distasonis* | |

Fig. 18

| Abbreviation | Anti-infective |
|---|---|
| ACV | aciclovir |
| AFG | anidulafungin |
| CAZ | ceftazidime |
| CFG | caspofungin |
| CIP | ciprofloxacin |
| CLI | clindamycin |
| CTX | cotrimoxazol |
| FLC | fluconazole |
| FLX | flucloxacillin |
| IPM | imipenem |
| LZD | linezolid |
| MEM | meropenem |
| MTZ | metronidazole |
| MXF | moxifloxacin |
| TGC | tigecycline |
| TZP | piperacillin-tazobactam |
| VAN | vancomycin |

Fig. 19

HUMAN PLASMA (K2 EDTA) (SEPSIS)

| Gender | Age | Organism |
|--------|-----|----------|
| Male | 59 | Staph Aureus |
| Male | 52 | Staph Aureus |
| Male | 38 | Bacillus Not Anthracis |
| Male | 55 | Strep Viridans Grp |
| Male | 51 | Staph Aureus |

METHOD AND DEVICE FOR NUCLEIC ACID BASED DIAGNOSTIC APPROACHES INCLUDING THE DETERMINATION OF A DEVIANT CONDITION, ESPECIALLY A HEALTH CONDITION AND/OR A PATHOGENIC CONDITION OF A SAMPLE

CROSS-REFERENCE TO RELATED APPLICATIONS

This is a National Stage application of PCT international application PCT/EP2016/071219, filed on Sep. 8, 2016, which claims the priority of EP Patent Application No. 15184688.8, filed Sep. 10, 2015, both of which are incorporated herein by reference in their entirety.

The present invention relates to a method and a device for a nucleic acid based diagnostic approach including the determination of a deviant condition of a sample, wherein the deviant condition is preferably a health condition and/or a pathogenic condition.

The reliable and fast detection and characterization of a deviant condition, especially health or pathogenic condition in a sample is of utmost importance for preventing the outbreak or treating a disease in a subject in need thereof. A health or pathogenic condition of a sample represents an indicator of a developing or already established disease, such as complex diseases or infections.

Infections remain a challenge in intensive care medicine. Within the last decades, the incidence of infections was shown to increase continuously. Despite massive efforts in research, new therapeutic approaches are rare and mortality in patients with infections still remains unacceptably high. In addition to an early focus control, recent guidelines recommend the initiation of an empiric antibiotic therapy as early as possible, preferably within one hour, following diagnosis of sepsis. However, the identification of the causative pathogen as well as its resistance pattern is crucial for an early optimization of the antimicrobial treatment regime. In this context, culture-based diagnostic procedures, for example blood cultures, are known to be the gold standard of care, although they are known to be associated with relevant disadvantages, in particular (i) depending on microbiological growth, it often takes up to 5 days until the results are available, and (ii) culture-based diagnostic procedures often reveal false negative results due to the administration of an empiric antibiotic therapy.

Accordingly, patients suffering from infections are at high risk for antimicrobial overtreatment, antibiotics-related toxicity and the selection of multi-drug resistant pathogens due to an inadequate and prolonged use of broad-spectrum antibiotics. In this context, culture-independent molecular diagnostic procedures, for example PCR-based techniques, were already introduced for the identification of the causative pathogen in infected patients. WO2012/135815 discloses a method for detecting a target nucleic acid derived from a pathogen in a subject. The method comprises (a) amplifying the nucleic acid sequence of the target nucleic acid, which is obtained from a cell-free fraction of a blood sample from the subject and (b) detecting the double stranded DNA. The presence of the double stranded DNA indicates the presence of the target nucleic acid in the subject.

However, the occurrence of ambiguous results as well as limitations in quantitative measures of the bacterial load in patients' samples and detection of antibiotic resistance markers are known weaknesses of these PCR-based diagnostic approaches. There are still uncertainties whether the identified organism is etiologic for an infection or whether there might be mixed infections. Although various targeted molecular tests for the identification of infections are available, time-consuming blood-culture approaches are still the gold standard.

The fast and efficient qualitative and quantitative detection and determination of a deviant condition, in particular the presence of a pathogen, for example microorganisms or viruses, in a subject is, thus, a big challenge in microbiological analysis and diagnostics. This is even more the case for analysis and diagnostics of the detection of a complete health or pathogenic status of a subject covering pathogens comprehensively, which prevents time-consuming analysis for many specific pathogens separately.

Thus, there is still a strong need for a fast and efficient diagnostic approach with sufficient sensitivity for identification of in particular infecting microorganisms and viruses in biological samples which are relevant for diseases.

The underlying technical problem of the present invention is to provide a method for quantitative and qualitative determination of deviant, especially health or pathological conditions, in particular relevant pathogens, in a subject, which overcomes the above-identified disadvantages and shortcomings, in particular which is a fast, efficient, reliable, precise and sensitive method for quantitative and qualitative determination of relevant pathogens in a subject.

The technical problem of the present invention is in particular solved by the subject-matter of the independent claims.

The present invention relates in particular to a method and a device for determination of a deviant condition of a sample, comprising the following steps, in particular consisting of the following steps:
  a) providing a sample comprising at least one specific nucleic acid from a sample source,
  b) providing a data base comprising at least one data set relating to the specific nucleic acid, which data set indicates the probability for the occurrence of at least one particular abundance of the specific nucleic acid in a control group,
  c) sequencing the at least one nucleic acid in the sample to determine the identity and abundance of the at least one specific nucleic acid in the sample,
  d) assigning the identity of the at least one specific nucleic acid determined in step c) to a data set of the data base provided in step b) which data set relates to the same specific nucleic acid determined in step c),
  e) computing a significance score indicating the deviant condition of the sample based on the abundance of the at least one specific nucleic acid of the sample determined according to step c) and the probability for the occurrence of the at least one particular abundance of the same specific nucleic acid provided in step b).

Preferably, the order of the process steps is a), b), c), d) and e) or, in another embodiment, is b), a), c), d) and e). In a further preferred embodiment, the data base according to step b) is provided after step c).

Preferably, the deviant condition is a health condition and/or a pathogenic condition.

Preferably, the deviant condition is a pathogenic condition. The present invention preferably relates also to a method for determination of a pathogenic condition of a sample, comprising the following steps:
  a) providing a sample comprising at least one specific nucleic acid from a sample source,
  b) providing a data base comprising at least one data set relating to the specific nucleic acid, which data set indicates the probability for the occurrence of at least one particular abundance of the specific nucleic acid in a control group, c) sequencing the at least one nucleic acid in the sample to determine the identity and abundance of the at least one specific nucleic acid in the sample, d) assigning the identity of the at least one specific nucleic acid determined in step c) to a data set of the data base provided in step b) which data set relates to the same specific nucleic acid determined in step c), e) computing a significance score indicating the pathogenic condition of the sample based on the abundance of the at least one specific nucleic acid of the sample determined according to step c) and the probability for the occurrence of the at least one particular abundance of the same specific nucleic acid in the control group provided in step b).

The present invention, therefore, provides a method for the determination of a deviant condition, preferably a pathogenic condition, of a sample according to which at least one specific nucleic acid present in a sample, the occurrence, abundance or occurrence and abundance of said specific nucleic acid is potentially indicative of a deviant condition, preferably pathogenic condition of said sample, is sequenced, is assigned to a data set of a data base which data set comprises data on the occurrence and abundance of the same specific nucleic acid in and/or of a nucleic acid relating to the specific nucleic acid in a control group, and wherein the data set relating to said specific nucleic acid derived from a control group is used to compute a significance score, wherein said significance score indicates the deviant, preferably pathogenic condition of the sample.

Thus, the occurrence, the abundance or both of the at least one specific nucleic acid present in the sample sequenced and identified in step c) is calculatory combined with knowledge provided by the data base according to step b) on the occurrence, the abundance or both of said specific nucleic acid or a nucleic acid related to the specific nucleic acid being present in a control group so as to indicate a deviant, preferably pathogenic condition, preferably being indicative for the occurrence of a pathogen in the sample. The data base provided in step b) provides at least one data set comprising data preferably informing on the occurrence and abundance and resulting therefrom on the probability of occurrence of a particular abundance, preferably of any abundance, of said specific nucleic acid and/or a nucleic acid related to the specific nucleic in a control group. The at least one data set provided in step b) enables preferably the assignment in step d) of a specific nucleic acid identified in step c) to the corresponding, i.e. the same or at least similar nucleic acid, or to a nucleic acid related to the specific nucleic identified in a control group, in particular allows it to assign the identity of the nucleic acid identified in step c) to the same or a least similar nucleic acid or to a nucleic acid related to the specific nucleic in a control group and thereby to a data set comprising data on the occurrence, abundance (also termed number or amount) or both of said nucleic acid in a control group.

In a preferred embodiment of the invention, the at least one data set relating to the specific nucleic acid refers to the specific nucleic acid or to a nucleic acid similar to the specific nucleic acid or to a nucleic acid derived from the same origin.

In a preferred embodiment the specific nucleic acid from a sample identified in step c) is assigned in step d) to a data set of a nucleic acid identified in a control group which has a similarity of at least 73%, preferably at least 75%, preferably at least 80%, preferably at least 85%, preferably at least 90%, preferably at least 95%, preferably at least 98%, more preferably is exactly the same. In a preferred embodiment the specific nucleic acid identified in step c) is assigned in step d) to a data set provided in step b) of the same species.

Alternatively the at least one data set provided in step b) enables preferably the assignment in step d) of a specific nucleic acid identified in step c) to at least one nucleic acid related to the specific nucleic acid identified in step c).

The at least one data set provided in step b) relates to the specific nucleic acid identified in step c). This means, that the at least one data set provided in step b) provides data about the specific nucleic acid from a sample identified in step c), about a similar nucleic acid and/or about a at least one nucleic acid related to the specific nucleic acid identified in step c).

A nucleic acid related to the specific nucleic acid identified in step c) is preferably a nucleic acid which has the same origin, especially the same specific and relatable origin, i.e. both are derived from the same origin, e.g. the same microorganism, virus, fungal organism or type of cancer cell.

The data base preferably provides information about the origin of the specific nucleic acid identified in step c). Furthermore the database preferably provides at least one data set, which data set indicates the probability for the occurrence of the at least one particular abundance of the specific nucleic acid in a control group. This dataset is based either on information about the specific nucleic acid identified in step c), and/or on information about a similar nucleic acid and/or on information about a nucleic acid related to the specific nucleic acid identified in step c).

Said assignment allows comparing the identity and abundance of the at least one specific nucleic acid found in the sample to the probability for the occurrence of said identified abundance for said identified specific nucleic acid in a control group and, in turn, allows providing a significance score indicating the significance for the identified and quantitatively determined nucleic acid in the sample for a deviant condition. In a preferred embodiment the data base is a nucleic acid data base, preferably the data base provides the probability distribution of at least one specific nucleic acid in a control group. In a preferred embodiment, the data base provides information about the deviant or pathogenic relevance of the specific nucleic acid.

Thus, the present invention uses data provided by the sequencing step c) on the occurrence, the abundance and/or the occurrence and abundance of at least one specific nucleic acid in a sample to determine a deviant, preferably pathogenic condition, wherein said determination further uses a data base provided in step b) comprising at least one data set relating to the specific nucleic acid, which data set indicates the probability for the occurrence of at least one particular abundance, preferably many abundances, preferably any abundance, of the specific nucleic acid in a control group. Determining the occurrence and abundance of a specific nucleic acid in a sample and comparing said data with the above-identified data contained in the data set derived from a control group, which data set comprises data on the probability for the occurrence of a multitude of abundances of said specific nucleic acid sequence found in the sample, including a probability for the occurrence of the identified abundance of the identified specific nucleic acid in the sample identified in step c), allows calculating a significance score, i.e. allows to conclude whether the occurrence, the abundance or the occurrence and abundance of said nucleic acid provided in the sample is relevant to a deviant, for example pathogenic condition or not. The more significant the occurrence, abundance or occurrence and abundance of the sequenced and identified at least one nucleic acid is in comparison with the occurrence, abundance or occurrence and abundance of said nucleic acid or a nucleic acid related to said nucleic acid in the control group, the more likely a deviant condition is existing.

In a preferred embodiment, the present invention provides a method for the determination of a deviant, preferably pathogenic condition of a sample, wherein at least one, preferably at least two, preferably at least three, preferably at least four, preferably at least five, preferably at least six, preferably at least 10, preferably at least 20, preferably at least 30, preferably at least 50, preferably at least 100 or preferably at least 200 or more or many nucleic acids, preferably at least 500, preferably at least 1000, preferably at least 5000, preferably at least 10000, preferably at least 50000, preferably at least 100000, from a sample source are sequenced in step c), assigned to at least one data set of the data base, in particular of a data base comprising at least a corresponding number of data sets each of them relating to a specific nucleic acid of a control group corresponding to the identified specific nucleic acid from the sample in step d) and a significance score is computed in step e).

In a further preferred embodiment, the present method sequences in step c) all nucleic acids in a sample, preferably all nucleic acids of non-human origin in a sample, then assigns the identities of said nucleic acids to a data set from a data base comprising at least a corresponding number of data sets each of them relating to a nucleic acid present in the control group corresponding to the identified specific nucleic acid from the sample in step d) and computes a significance score in step e).

The method of the present invention is, thus, advantageously able to sequence and assign an identity to all nucleic acids of a sample.

Advantageously, the method of the present invention combines a quantitative detection of at least one nucleic acid in a sample, i.e. a determination of its abundance in the sample, with a probabilistic interpretation of the abundance of said at least one nucleic acid, which abundance is preferably indicative for at least one microorganism, virus and/or cancer cell in a sample, preferably which abundance is increased in comparison to control group, preferably a healthy control group. The abundance of different species, preferably pathogens, in a sample can be compared to a control group and, accordingly, the relevance of a defined species, preferably pathogen, for the deviant, preferably pathogenic condition can be determined since the mere presence of a pathogen is not always and inevitably responsible or caused by a disease. The method also provides information about the quantity of all microorganisms, viruses and/or cancer cells, preferably pathogens, in a sample and indicates the abnormality of the deviant condition, preferably the abnormality of a specific pathogen, represented by an abnormal occurrence or abnormal abundance of occurrence.

The workflow as per the present invention advantageously identifies a condition of a subject without previous indication based on data analysis which does not require specific primer design, and provides the opportunity to detect microorganisms, viruses and/or cancer cells, and the deviant condition of a subject in a single assay.

The workflow as per the present invention especially identifies a condition of a subject without previous indication based on data analysis which does not require specific primer design, and provides the opportunity to detect pathogens, preferably bacterial, fungal and viral pathogens, and the health condition of a subject in a single assay. Accordingly, the method of the present invention preferably determines a deviant condition, in particular relevant pathogens, in a sample by combining a qualitative and quantitative analysis of nucleic acids and assigning significance thereto.

Advantageously, the method allows a fast, efficient and sensitive determination of a deviant condition, in particular of relevant pathogens, preferably of infectious pathogens, in a subject by providing a complete diagnostic workflow based on unbiased sequence analysis of nucleic acids. In preferred embodiments, the method allows the determination of a deviant condition in a sample, which deviant condition is characterized by the occurrence of a number of different pathogens in a sample, which allows identification of mixed infections.

The present method is providing information whether the identified microorganism, virus and/or, preferably pathogen, is relevant for an infection or contamination by including quantitative results, which are assessed by comparing them with results obtained from a control group and wherein organisms relevant for an infection or contamination are determined. This efficient and specific identification of at least one pathogen is not depending on culturing microorganisms for several days and, thus, is much faster. There is no risk that a potential pathogen will not be detected and identified due to the selection of not appropriate growing conditions. Furthermore, the present method considers not only occurrence, means qualitative occurrence, i.e. whether a pathogen is detectable or not, but also abundance of a pathogen which allows a rating whether the abundance of occurrence of such a pathogen does actually indicate a potential deviant condition, preferably a potential pathogenic condition. The coverage of a bunch of potential pathogens does also allow identifying several diseases, which occur in a subject simultaneously, e.g. mixed infections. This is in particular important for diagnosis of a subject without a reliable symptom indication and therefore it is not clear at the beginning for which microorganisms, viruses or disease to look for.

In accordance with the present invention, an improved method, preferably diagnostic method, and device for the determination of a deviant condition, for example caused by infectious microorganisms, based on unbiased sequence analyses of nucleic acids, preferably free circulating DNA (cfDNA), from samples, preferably plasma samples, of patients, for example infected patients, preferably by sequencing, more preferably by high-throughput sequencing, for example next generation sequencing (NGS), is provided. The suitability of the present teaching for early detection and monitoring of bacteremia in seven infected patients, six non-infected patients following major abdominal surgery as well as twelve healthy volunteers serving as controls in comparison to blood culture-based analytic procedures is described herein. Moreover, the ability of the present teaching for the detection of antibiotic resistance markers is shown. The complete workflow from sample preparation to species identification report could be accomplished in about 30 hours making the method of the present invention a powerful diagnostic tool for critically ill patients suffering from infections. The results of the method can improve, with regards to reliability and time, in line with the improvement of sequencing methods and number of available data sets. It has been surprisingly found that levels of nucleic acids, preferably free circulating DNA, were significantly higher in infected patients and non-infected post-surgery controls, but not in healthy controls. The method permits an absolute comparison between different microbial species found in one sample. Accordingly, besides the data-driven identification of pathogens in clinical specimens this method is also highly useful in monitoring the bacterial load of a subject and response to targeted treatment and complement standard clinical microbiology.

Figure 5:
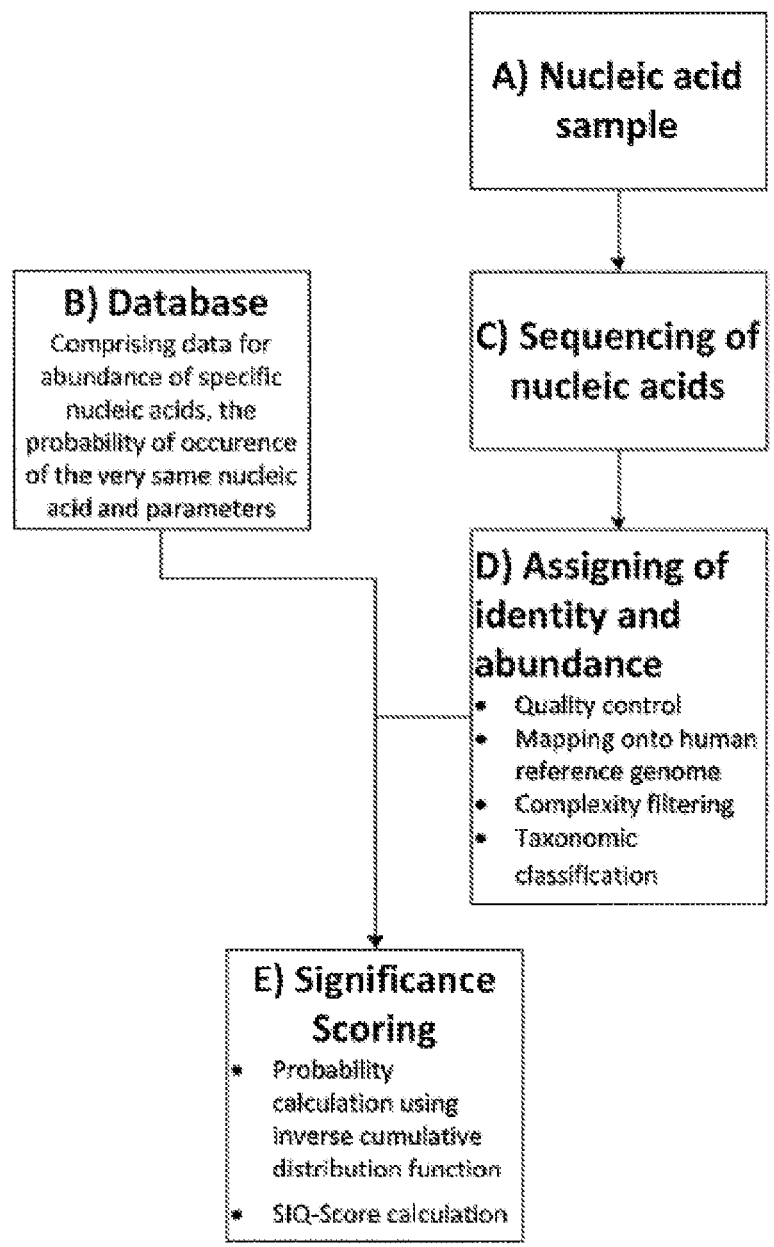

FIG. 5 schematically outlines the present method for the determination of a deviant condition of a sample comprising in step a) providing at least a specific nucleic acid containing sample, providing in a step b) a data base which comprises data on the abundance of specific nucleic acids, in particular probabilities for the occurrence of the same nucleic acid as identified in step c), in particular a probability for the occurrence of the identified abundance, and optionally further parameters for said nucleic acid and in step c) sequencing the at least one specific nucleic acid in the sample including determining its abundance and in step d) assigning the identity of the at least one specific nucleic acid determined and quantified in step c) to a corresponding data set of the corresponding same nucleic acid being comprised by the data base provided in step b) and whereby in a step c) a significance score, i.e. a value indicating the significance of the occurrence and abundance of the sequenced nucleic acid in the sample using probability calculations, in particular using the logarithm of reciprocal cumulative distribution functions so as to preferably provide a SIQ score calculation resulting in a SIQscore (significance identifying quantifier).

In a preferred embodiment, during or subsequent to process step d), the present process may comprise a process step analyzing the quality of the sequenced at least one specific nucleic acid in the sample and/or a process step according to which the at least one identified nucleic acid in step c) is mapped onto the human reference genome and/or a process step of complexity filtering the obtained data on the nucleic acid sequences and/or a further optional process step of a taxonomic classification of the identified at least one specific nucleic acid.

In a preferred embodiment, a statistical estimator, preferably a Maximum Likelihood Estimation (MLE), for every specific nucleic acid potentially indicative for a specific pathogen identified in step c) is calculated in step e), which preferably estimates the probability to detect a specific pathogen, preferably the abundance thereof, in a control group or a control sample, wherein preferably the distribution, most preferably the Poisson distribution, preferably derived from the healthy individuals, with pathogen-specific parameters is computed and compared to the abundance of the specific nucleic acid present in the sample which is sequenced in step c).

In a preferred embodiment, the result of the present determination method provided in step e) comprises an interpretation and optionally a visualization of the results for preferably all microorganisms, viruses, cancer cells and/or pathogens found in a sample and is provided as a significance score, preferably the SIQ score. The significance score is computed integrating the abundance of the specific nucleic acids in the sample and the significance of the abundances of the specific nucleic acids for all microorganisms, viruses, cancer cells and/or pathogens, preferably the probability of occurrence of said specific nucleic acids in the control group, wherein normalized data on the amount of identified nucleic acids were compared for each microorganisms, viruses, cancer cells and/or pathogens between the subject and controls. The significance score is indicating the deviant condition of a sample, preferably indicating the relevant pathogens in a sample.

Definitions

In the context of the present invention, the term 'deviant condition' means a health condition and/or a pathogenic condition, preferably a condition with characteristics varying from what is considered standard or normal, preferably which is varying from a control group. In a preferred embodiment, the deviant condition is characterized by the occurrence of a specific nucleic acid or by deviant or abnormal quantities of a specific nucleic acid, e.g. pathogenic quantities of a specific nucleic acid.

In the context of the present invention, the term 'pathogenic condition' means a condition which indicates the development or/and occurrence of a particular disease, in particular, is associated with the development or/and occurrence of a particular disease. In the context of the present invention, the term 'pathogenic condition' in particular means a condition which indicates the occurrence, the abundance or the occurrence and the abundance of a specific nucleic acid in a sample which occurrence, abundance or occurrence and abundance is indicative for the development or occurrence of a particular disease, namely is always, regularly or likely associated with a particular diseases and which is not found or found significantly less frequently in a control group.

In a preferred embodiment, the pathogenic condition is characterized by the occurrence of at least one specific nucleic acid or by pathogenic quantities of at least one specific nucleic acid.

In the context of the present invention, the term 'health condition' in particular means a condition which indicates the occurrence, the abundance or the occurrence and the abundance of a specific nucleic acid in a sample which occurrence, abundance or occurrence and abundance is indicative for the microbiome, an environmental condition and/or a lifestyle condition, preferably a condition that does not cause or produce disease, preferably a non-pathogenic condition. In a further embodiment the health condition is indicative for a complex disease or a pathogenic disease.

In the context of the present invention, the term 'lifestyle' is the habits, attitudes, tastes, moral standards, economic level, etc., that together constitute the mode of living of an individual or group.

In the context of the present invention a 'complex disease' is a disease, preferably such as heart disease, diabetes, cancer and obesity, which is linked with the effects of multiple genes and sometimes in combination with lifestyle and environmental factors.

In the context of the present invention a 'disease' is an abnormal condition of a subject, in particular a disorder of a structure or function, affecting a part or all of an organism. The disease may be caused by factors originating from an external source, such as an infectious disease, or it is caused by internal dysfunctions, such as an autoimmune disease or genetic disorders. In a preferred embodiment, a disease is a disease characterized by the occurrence of nucleic acids of pathogens, in particular by the occurrence of pathogens. Such a disease is also called an infectious disease.

In the context of the present invention, the term 'pathogen' preferably refers to an infectious agent, preferably an agent such as a virus, bacterium, fungus, viroid, or parasite that causes disease.

In a preferred embodiment of the present invention, a disease can be an infectious disease, in particular a disease caused by living agents, preferably caused by a bacterium, fungus and/or a parasite, or by viruses or viroids, in particular a sepsis. In a furthermore preferred embodiment, the disease is a complex disease, for example cancer.

In a preferred embodiment the infectious disease can be caused by an infectious agent, in particular a living agent, which includes, but is not limited to, bacteria, fungi, parasites, yeasts, protozoa, helminths and insect larval stages and other nucleic acid containing agents including viruses and viroids.

In a preferred embodiment, the disease is selected from autoimmune disorders, airway inflammation, inflammatory disorders, asthma, arthritis, transplant rejection, infectious disease, cancer, Lyme disease, ocular infections, skin disorders, psoriasis, scleroderma, cardiovascular disease, atherosclerosis, chronic fatigue syndrome, sarcoidosis, or another disease.

In a preferred embodiment, the deviant condition is characterized by the occurrence of a specific nucleic acid indicative for a complex disease, especially cancer, in particular indicative for cancer cells, or by the occurrence of relevant quantities of nucleic acids indicative for cancer or for cancer cells.

In a preferred embodiment of the present invention, in which the deviant condition determined indicates an infectious disease, for instance caused by pathogens, total nucleic acids, preferably DNA, is isolated from a subject, provided in form of a sample in step a), and sequenced in step c), wherein from the sequencing results, human DNA is removed, for instance after mapping to human genome and unmapped nucleic acids are further processed in step d). In a preferred embodiment the specific nucleic acid provided in step a) is enriched prior to step c) or after step c), preferably between step c) and d).

If an enrichment step is used the nucleic acid of the control group is preferably treated by the same enrichment step.

In a preferred embodiment, from the unmapped nucleic acids, preferably a pathogen, the infectious disease causing agents, such as microbial species, are classified and nucleic acids are normalized, counted and sorted by their abundance and then processed in step d). For each specific nucleic acid identified in a subject, results are compared in steps d) and e) to likewise processed samples of uninfected controls, wherein microbial species identified in the sample as well as in uninfected controls are considered as non-relevant for pathogenesis. If a microbial species is found in high abundance only in the sample and in none of the uninfected controls a high significance is assigned and consequently a high SIQ score, indicated by the radius of its datapoint in the SIQ plot (FIGS. 2A and E). For pathogens that are not common the SIQ score will be higher than those that are often detected in the control group.

In a preferred embodiment, the deviant condition is characterized by the occurrence or by the presence of pathogenic quantities of nucleic acids, in particular genes, indicating an antibiotic resistance. Thus, the present invention considers the occurrence, in particular a particular abundance, of nucleic acids indicative for an antibiotic resistance to be a deviant condition.

In context of the present invention, the term 'antibiotic resistance' means a loss of susceptibility of bacteria to the killing, or growth-inhibiting properties of an antibiotic agent. It also relates to resistance of a microorganism to an antimicrobial drug that was originally effective for treatment of infections caused by it. Resistant microorganisms, including bacteria, fungi, viruses and parasites, are able to withstand attack by antimicrobial drugs, such as antibacterial drugs, antifungals, antivirals, and anti-malarials, so that standard treatments become ineffective and infections persist.

In the context of the present invention, the term 'healthy' is meant to refer to subjects which do not display any signs of a particular disease, and preferably which currently are not developing said disease, preferably the subjects are considered to be healthy.

In the context of the present invention, a control group is a group of samples from a group of subjects which are healthy or considered to be healthy. The control group comprises at least one sample from at least one subject, preferably a large number of samples from a large number of subjects, such as at least 10, at least 20, at least 30, at least 50, at least 100, at least 1000 or at least 5000, samples from a corresponding number of healthy subjects. Preferably, one control sample originates from one healthy subject. A larger number and a higher diversity of control samples in a control group raise the probability of capturing all possible species which has an effect on the variability introduced through contamination. In general, the reliability of the presently provided significance score, preferably SIQ score, is increased by using the most complete database of relevant genomes and a large control group as possible to capture small varieties in the microbiome of healthy individuals and/or to exclude contaminating organisms.

Thus, the term 'control group' means at least one control sample from a subject in a healthy condition which is not suffering from a disease, preferably the control group comprises a group of control samples from healthy individuals that match the patient group in a variety of ways, for example, they might be of similar age and gender, the same social class or the same ethnic group. The present invention preferably relates to a method, wherein the control group is characterized by a non-pathogenic condition. The present invention preferably relates to a method, wherein the control group is characterized by an indication specific condition.

The term 'subject' refers to a mammalian organism, mammals generally include, but are not limited to, humans, non-human primates, rats, mice, cats, dogs, horses, cows, pigs, sheep and rabbits. In a preferred embodiment the subject is a human.

In context of the present invention, the term 'sample source' means any source of at least one nucleic acid, in purified or non-purified form, preferably the sample source is an organism, preferably a human organism, preferably the sample source is screened for or suffering from a deviant condition.

In context of the present invention, the term 'nucleic acid' comprises nucleic acids or nucleic acid fragments, for example, DNA or RNA, including messenger RNA, which DNA or RNA may be single stranded or double stranded or mixtures thereof, preferably the nucleic acid is a free circulating DNA or RNA. In one embodiment, the term 'nucleic acid' is also understood to mean 'nucleic acid sequence'.

In context of the present invention, the term 'sequencing' means to determine the primary structure of an unbranched biopolymer, preferably to determine the sequence of at least one nucleic acid, it includes any method that is used to determine the order of the bases in a strand of at least one nucleic acid, preferably high-throughput sequencing.

In context of the present invention, the term 'high-throughput sequencing' means sequencing technologies that parallelize the sequencing process, preferably means sequencing a large number of sequences concurrently in a single run, preferably next-generation sequencing (NGS), Ilummina, IONTorrent or NanoPore sequencing. The sequencing in step c) is preferably performed by molecular high-throughput sequencing preferably next generation sequencing.

In context of the present invention, the term 'data base' relates to an organized collection of data comprising at least one data set, preferably as an electronic filing system, preferably collected from medical records, scientific experiments, published literature, clinical studies, high-throughput experiment technology, and computational analysis. The data base according to step b) is preferably retrieved from clinical studies, preferably collected from a defined control group. In a preferred embodiment the data base is generated for a defined indication, preferably from published data, preferably from a selected control group characterized by a specific condition. In another preferred embodiment the data set indicates the probability for the occurrence of at least one particular abundance of the specific nucleic acid or a fragment thereof in a control group.

In a preferred embodiment, the data base therefore comprises at least one, in particular more than 10, in particular more than 20, in particular more than 50 or in particular more than 100, in particular more than 200 or in particular more than 1000 data sets, whereby each single data set is assigned to a particular nucleic acid having a particular identity, e.g. characterizing a specific species, variety or mutant.

In a preferred embodiment, the data base comprises at least 5, at least 10, at least 20, at least 30, at least 40, at least 50, at least 60, at least 70, at least 80, at least 90, at least 100, at least 200, at least 300, at least 500, at least 1000 at least 10,000, at least 100,000 or even more, data sets for specific nucleic acids, preferably for a specific nucleic acid from a defined origin.

In context of the present invention, the term 'data set' means data relating to a specific nucleic acid and wherein these data inform on the occurrence, i.e. the presence, the abundance, i.e. the frequency, number or amount, or on the occurrence and abundance of the specific nucleic acid in a control group. In a preferred embodiment, these data on the occurrence, abundance, occurrence and abundance are data on the probability for the occurrence of at least one, preferably more, preferably numerous, abundances of said specific nucleic acid in a control group. Preferably, the data set comprises data indicating the probabilities for the occurrence of all conceivable abundances of a specific nucleic acid in a control group. In a preferred embodiment the at least one data set is standardized with respect to an indication specific control group.

In the context of the present invention, the term 'abundance' means the number, in particular amount or frequency, of a specific nucleic acid present in a sample, preferably identified in a sample.

In the context of the present invention, the term 'probability for the occurrence' means the probability to find a particular abundance of a specific nucleic acid in a control group.

In context of the present invention, the term 'significance score' means a value which quantitatively indicates the likelihood for a deviant condition of a sample, preferably by combining the determined abundance of a specific nucleic acid in a sample and the probability for the occurrence of the at least one determined particular abundance of the same specific nucleic acid in a control group. In a preferred embodiment the significance score (SIQ score), the significance identifying quantifier, ranks and selects nucleic acids which are potentially pathogenic, responsible for a deviant condition or generated due to a deviant condition. Preferably the SIQ score is indicating a specific disease and more preferably the SIQ score indicates the relevance of a specific deviant condition, in particular a pathogen, for one or several diseases. The SIQ score preferably discriminates at least one specific nucleic acid which might be relevant from noise caused by contaminant or commensal species and quantitatively evaluates the at least one specific nucleic acid. In a preferred embodiment the significance score (SIQ score) is a sepsis indicating score.

In context of the present invention, the term 'read' means a specific nucleic acid for which the nucleotide sequence has been determined by sequencing and which is preferably assigned to an organism, preferably mapped to the genome of the respective organism. In a preferred embodiment, the reads are classified to specific organisms, preferably classified to specific microorganisms, preferably normalized and sought by their abundance.

The present invention in a further embodiment relates to a method for diagnosis of a deviant condition or a disease in a subject, wherein a method for determining a deviant condition of a sample in said subject according to the present invention is carried out.

In a preferred embodiment, the invention provides a method for monitoring the infection status of a subject, preferably for monitoring a subject during treatment and response to therapy, wherein a method for determining a deviant condition of a sample of said subject according to the present invention is carried out.

Such methods preferably relate to the identification of a subject suffering from a disease, preferably to a screening for a disease, preferably to a preventive medical analysis. In a preferred embodiment such methods identify correlation of the occurrence of a pathogen and the development of a disease in a subject.

The present invention preferably relates to a method, wherein the sample is obtained from a sample source selected from the group consisting of whole blood, serum, blood plasma, liquor, urine, tissue, sputum, faeces and lavage, preferably from a cell-free fraction of the blood plasma. The sample can be collected using any of the standard methods known in the art.

According to the invention, the sample is obtained from a human or animal body. In accordance with the present invention, said sample is analysed according to the present method and during the method or thereafter not returned to the human or animal body. In accordance with the present invention, the present method for determination of a deviant condition or the present method for the diagnosis of a deviant condition, thus, merely uses a sample obtained from a body and does not require the presence of the human or animal body.

In a preferred embodiment, the sample is blood plasma. In a preferred embodiment the sample can be obtained directly from the sample source. Blood plasma as presently used is preferably cell-free, preferably mainly cell-free. The sample, preferably blood plasma, may contain free circulating nucleic acids, comprising human nucleic acids and non-human nucleic acids.

In a preferred embodiment the sample can be diluted or concentrated. In another preferred embodiment the sample is processed prior to sequencing, preferably the sample is purified prior to sequencing. The sample may contain more than one desired specific nucleic acid sequence which may be the same or different.

In one embodiment of the present invention, the sample may contain in addition to the at least one specific nucleic acid further substances, e.g. further nucleic acids, in particular nucleic acids which are not indicative for a deviant condition.

The present invention preferably relates to a method, wherein the pathogenic condition is characterized by abnormal, especially pathogenic quantities of nucleic acids of at least one viral, bacterial, fungal or parasitic organism.

The present invention preferably relates to a method, wherein the deviant condition is characterized by deviant quantities of rejected cells of an implant.

The present invention preferably relates to a method, wherein the deviant condition is characterized by the presence of at least one gene which is indicative for an antibiotic resistance, preferably of at least one antibiotic resistance gene. In a preferred embodiment, such a deviant condition is determined simultaneously to another deviant condition of a subject.

In a preferred embodiment, the quality of at least one specific nucleic acid sequence identified in step c) is classified in a further process step, preferably in step c), preferably after step c), more preferably between step c) and d).

Thus, in a preferred embodiment of the present invention, the present method further employs a classification step, in particular a classification step allowing differentiating specific nucleic acids indicative for a disease from nucleic acids not being of interest in the present method.

In a preferred embodiment, in an optional classification step, the at least one specific nucleic acid is classified by its origin, preferably classified to an organism, preferably taxonomical classified, preferably classified as human or non-human, preferably classified as deviant or non-deviant, preferably classified to be indicative for pathogens or non-pathogens.

The present invention preferably differentiates, in an optional classification step, preferably conducted in step c) or d), or between steps c) and d), between nucleic acids originating from non-relevant, e.g. human source, and nucleic acids originating from all other organisms, preferably bacteria, viruses, fungi and parasites. By calculation of the significance of the deviation the method can differentiate between nucleic acid originating from a relevant source for the deviant condition, e.g. nucleic acids from microorganisms involved in the infection and nucleic acids of the normal human flora.

The present invention preferably differentiates, in an optional classification step, preferably conducted in step c) or d), or between steps c) and d), between nucleic acids originating from non-relevant, e.g. non-pathogenic organisms, e.g. from normal skin flora, and nucleic acids originating from relevant, e.g. pathogenic organisms, preferably the method differentiates between nucleic acids originating from an infection and nucleic acids from microorganisms of the human flora.

The present invention preferably differentiates, in an optional classification step, preferably conducted before step c), in step c) or d), or between steps c) and d), between nucleic acids originating from non-relevant origins, e.g. human nucleic acid, and relevant nucleic acid, e.g. nucleic acids originating from microorganisms, viruses or cancer cells.

In a preferred embodiment, the at least one nucleic acid is classified by aligning its sequence to a nucleic acid sequence, preferably to a known nucleic acid sequence, which nucleic acid sequence provided in a further, namely a second data base. The classification of nucleic acid sequences can be done by any method known in the art. In a preferred embodiment the specific nucleic acid is classified by mapping its sequence to reference genomes, preferably to the human genome.

In one embodiment of the present invention, the sample may contain in addition to the at least one specific nucleic acid further nucleic acids, in particular those which are not indicative for a deviant condition. In a preferred embodiment of the present invention, nucleic acids not indicative for a deviant condition, preferably a pathogenic condition, are depleted, i.e. removed from the sample, preferably after step a) and before step c) or during step c).

In a furthermore preferred embodiment of the present invention, nucleic acid sequences which are not indicative for a deviant condition, in particular which have been subjected to a classification step, indicating that the nucleic acids are not indicative for a deviant condition are depleted from the sample.

In a preferred embodiment, the nucleic acid sequences obtained in step c) are processed in step d), preferably in a bioinformatic workflow, which pre-selects non-relevant nucleic acids, preferably classifies remaining nucleic acids and indicates which nucleic acids are potentially relevant for a deviant condition. Finally, the result is obtained in step e) in form of a significance score (SIQ score), preferably by indication of a proprietary score which indicates the relevance of the identified nucleic acids for a deviant condition. In a preferred embodiment, the significance score, preferably the SIQ score, and preferably a corresponding SIQ plot, is obtained as schematically represented in FIGS. 2A and E.

Suitable biotechnical steps for enriching or depleting are known to the person skilled in the art.

In a preferred embodiment, the nucleic acid present in the sample is depleted or enriched, preferably the nucleic acid is depleted or enriched in the sample and the control group, preferably after step c), preferably before step e), preferably by using bioinformatic methods. In a preferred embodiment, the nucleic acid present in the sample is depleted or enriched before step c), preferably by using a biotechnological process step. In a preferred embodiment, nucleic acids present in the sample, which are specific nucleic acids and are indicative for a particular deviant condition, are, if desired, enriched.

In a preferred embodiment the at least one specific nucleic acid, preferably the classified specific nucleic acid, preferably a human or a non-pathogenic nucleic acid, is depleted or enriched, preferably sorted out from identified specific nucleic acids in the sample of step c), preferably human or non-pathogenic specific nucleic acids are sorted out, wherein the at least one specific nucleic acid is depleted or enriched in the sample and the control group. In a preferred embodiment the amount of different specific nucleic acids is depleted or enriched, preferably the abundance of specific nucleic acids obtained in step c) is depleted, preferably to reduce the complexity of the identified specific nucleic acids.

In a preferred embodiment of the present invention, nucleic acids are enriched or depleted, preferably by using biotechnological process steps, or using bioinformatic methods. In a preferred embodiment nucleic acids are depleted by removing nucleic acids of non-relevant species or human origin. In a preferred embodiment the at least one specific nucleic acid is depleted or enriched by filtering at least one specific nucleic acid based on at least one data set provided in step b).

The present invention preferably relates to a method, wherein nucleic acids are enriched prior to step c).

The present invention preferably relates to a method, wherein nucleic acids which potentially indicate a deviant condition are enriched prior to step c).

The present invention preferably relates to a method, wherein nucleic acids which potentially not indicate a deviant condition are depleted prior to step c).

In a preferred embodiment, the nucleic acid present in the sample is not depleted or enriched using biotechnological process steps. Advantageously such biotechnological process steps for depletion or enrichment are not mandatory in the method according to the present invention.

If an enrichment or depleting step is used, the nucleic acid of the control group is preferably treated by the same enrichment or depleting step.

The present invention relates also to a device for carrying out the method according to the present teaching, wherein a significance score indicating the deviant condition of the sample is computed based on the abundance of the at least one specific nucleic acid determined according to step c) and the probability for the occurrence of the at least one particular abundance of the same specific nucleic acid in the control sample provided in step b) by a central processing unit of the device.

In a preferred embodiment the significance score of at least one nucleic acid in the sample is computed in the processing unit of a sequencing device.

Accordingly, the present invention provides a complete diagnostic workflow for the identification of infectious organisms in a sample based on unbiased sequence analysis of nucleic acids, in particular free circulating DNA. The method advantageously provides a data-driven diagnosis without premonition of suspected species, does not require specific primer design, and provides the opportunity to detect bacterial, fungal and viral pathogens in a single assay.

The method of the present invention is preferably not restricted to the determination of a specific pathogen. In one embodiment, the present method determines the sum of potential pathogens, e.g. viral, bacterial, fungal or parasitic.

Thus, the present invention provides a useful method for identification of diseases in a subject and its corresponding medical cause within short time.

Thus, an appropriate therapy for the identified deviant condition can be selected within short time.

Accordingly, this method can be highly useful for data-driven identification of pathogens in clinical specimens and for monitoring the bacterial load of a subject and the response to targeted treatment and complement standard clinical microbiology.

Preferred embodiments of the present invention are the subject-matter of the dependent claims.

The sequence listing shows the following:
Seq ID 1: nucleic acid sequence mecA of *Enterobacter cloacae*
Seq ID 2: nucleic acid sequence SX2_r1 from human plasma sample 1
Seq ID 3: nucleic acid sequence SX2_r2 from human plasma sample 2
Seq ID 4: nucleic acid sequence SX2_r3 from human plasma sample 3

The present invention is illustrated by the following figures and examples.

The figures show:

FIG. 1: shows the Distribution of cfDNA concentrations over different patient groups and timepoints.

(A) Comparison of cfDNA concentrations between healthy volunteers (V), septic patients at the onset of sepsis (S T0), and non-infected patients following major abdominal surgery (P). (B) Alterations in cfDNA concentrations of septic patients' plasma samples collected over the observational period of the trial. Samples were obtained at sepsis onset (T0), after 24 hours (T1), 4 days (T2), 7 days (T3), 14 days (T4) and 28 days (T5). Note that for patient S60 T5 refers to day 21 and T6 refers to day 28 after sepsis onset. (C) Comparison of cfDNA concentrations in patients undergoing major abdominal surgery without evidence of infection. Blood samples from the postoperative group were collected prior to surgery (T0), immediately following the end of the surgical procedure (T1), and 24 hours later (T2).

Figure 2:
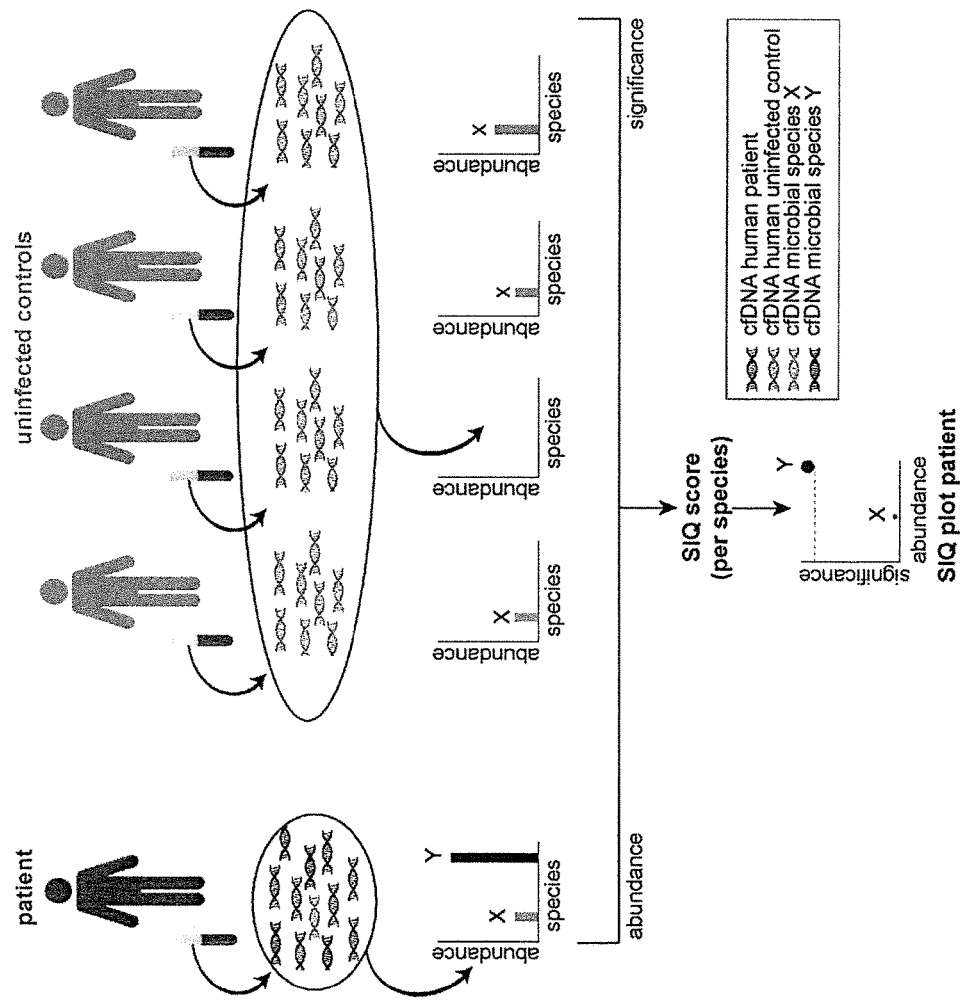
Figure 2:
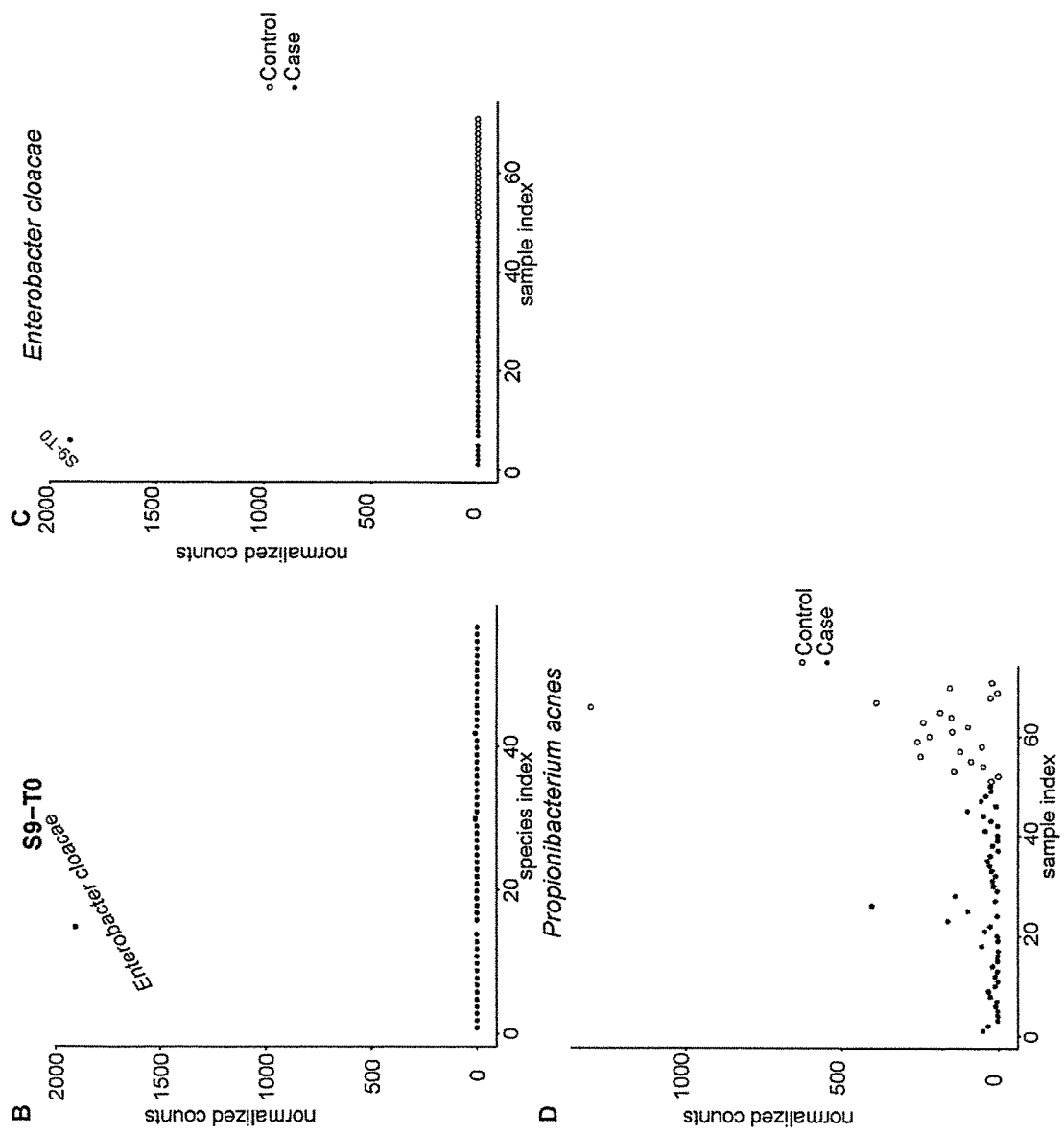
Figure 2:
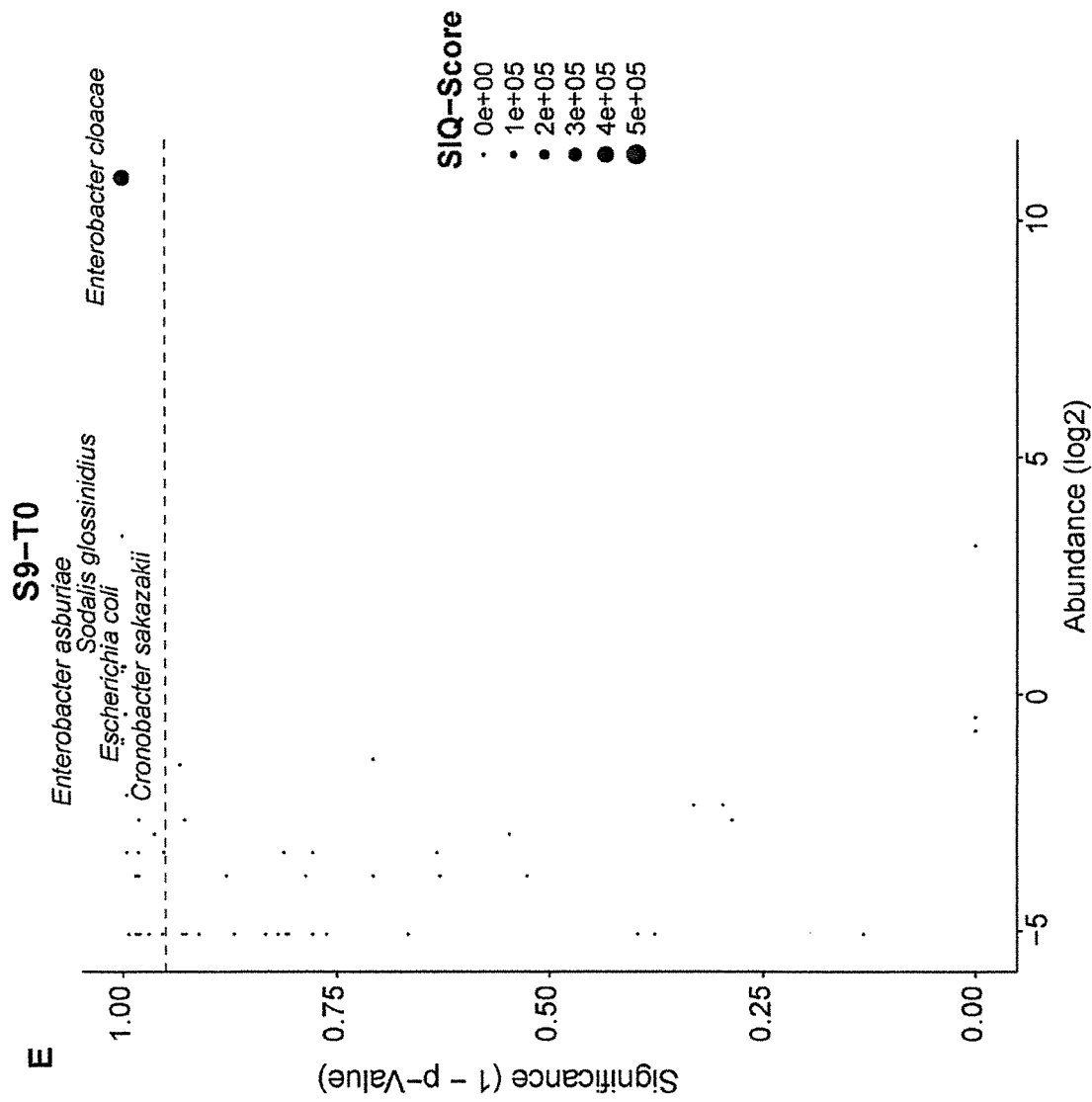

FIG. 2: shows rationale of SIQ score and SIQ plot.

(A) Outline for obtaining a SIQ score and SIQ plot. Total cfDNA is isolated from a patient's plasma and sequenced. From sequencing results, human cfDNA are removed after mapping and only unmapped reads are further processed. From these unmapped reads, microbial species are classified and reads are normalized, counted and sorted by their abundance. For each species obtained from a patient, results are compared to likewise processed samples of uninfected controls. In this example, microbial species X is found in the patient's sample as well as in most control samples, and therefore represents a contaminant or a member of the common human microbiome.

However, species Y is found in high abundance only in the patient's sample and in none of the controls and therefore receives a high significance and consequently a high SIQ score, indicated by the radius of its datapoint in the SIQ plot.

(B) Distribution of normalized counts for each species found in the plasma sample of patient S9 at the onset of sepsis (T0). Only the most abundant species *Enterobacter cloacae* was labeled.

(C) Distribution of the normalized counts for *Enterobacter cloacae* over all samples was analyzed. closed: septic patients, open: controls (elective surgery and healthy volunteers). Only sample S9 with the most abundant *E. cloacae* reads was labeled.

(D) Distribution of the normalized counts of *Propionibacterium acnes* over all samples. closed: septic patients, open: controls (elective surgery and healthy volunteers).

(E) SIQ plot integrating abundance and significance of all species for patient S9 at the onset of sepsis (T0). Coordinates of the data points (species) are the relative abundance (log 2) on the x-axis and the significance expressed as 1-p-value on the y-axis. The dashed line marks a p-value of 0.05. Datapoints with log 2>0 and p-value <0.05 are labeled. The SIQ score of a species in the respective sample is integrated as the radius of the datapoint.

Figure 3:
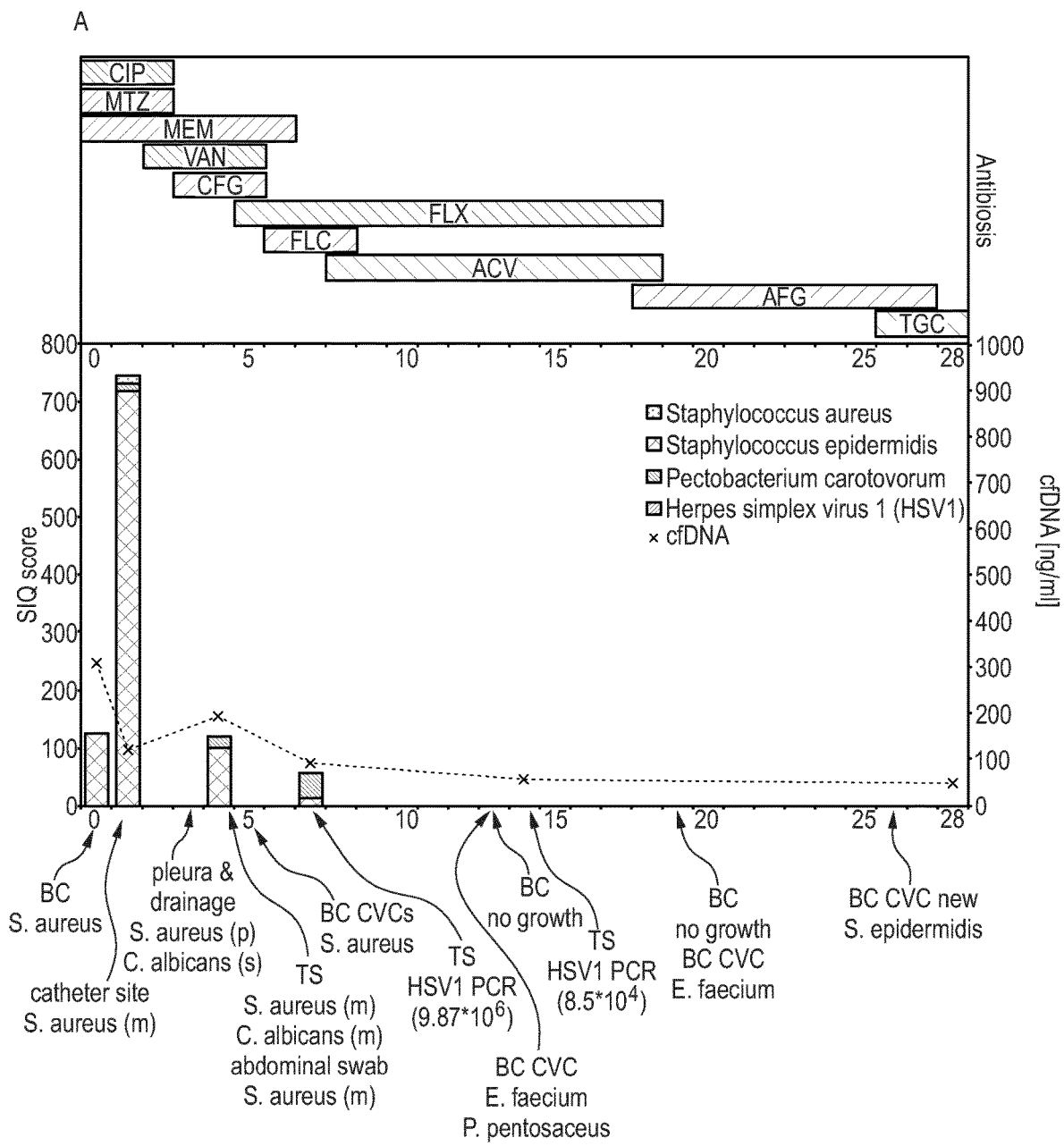
Figure 3:
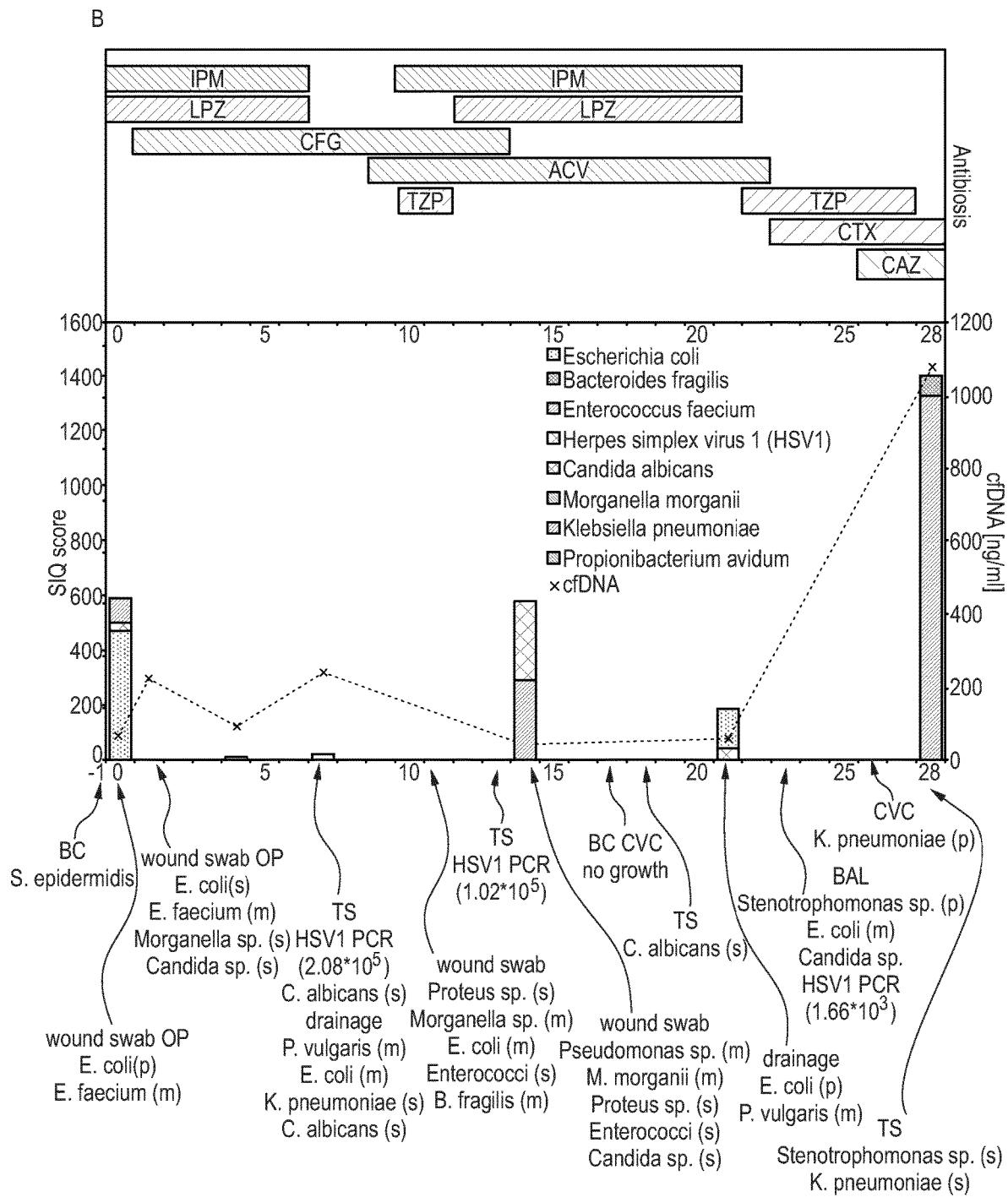

FIG. 3: shows clinical time courses including NGS data and conventional clinical microbiology data for two patients.

(A) Time course patient S10. A 68 year old male patient presented with a tumor of his stomach with the need for a gastrectomy. Following surgical procedure the patient suffered from septic shock due to severe pneumonia without any evidence for an anastomosis insufficiency. *Staphylococcus aureus* was shown to be the dominant organism in different secretions (e.g. tracheal secretion, abdominal wound swab, blood culture, etc.). Based on its methicillin-susceptibility, the patient was then treated with flucloxacillin for two weeks. In addition, pneumonia was shown to be accompanied (respectively boosted) by reactivation of herpes simplex virus type 1 (HSV1) in tracheal secretions, so that the patient received acyclovir for eleven days. Following a prolonged weaning phase, the patient was then able to be discharged to normal ward six weeks after the onset of septic shock. In this figure, the antibiotic treatment regime, SIQ scores for species identified via NGS/SEPseq and cfDNA concentrations of the respective plasma samples are plotted over the timeline of the trial period for patient S10. Pertinent (clinical microbiology) laboratory results are marked by arrows to the day the clinical specimen was obtained. The following abbreviations were used: blood culture (BC), central venous catheter (CVC), tracheal secretion (TS), herpes simplex virus (HSV), ciproflocaxine (CIP), metronidazole (MTZ), meropenem (MEM), vancomycin (VAN), caspofungin (CFG), flucloxacillin (FLX), fluconazole (FLC), aciclovir (ACV), anidulafungin (AFG), tigecycline (TGC). Anti-infectives are displayed as antibacterial antibiotics, antimycotics and antivirals in light grey, black and dark grey, respectively. The relative amount of bacteria found by conventional clinical microbiology is indicated with plenty (p), medium (m) or scarce (s). For a detailed list of anti-infectives abbreviations, see FIG. 18.

(B) Time course patient S60. Following a complicated course of perforated sigmoid diverticulitis, a 70 year old female patient presented for reconstruction of bowel continuity. In the postoperative phase the patient developed septic shock due to bowel leakage with the need for surgical revision. Abdominal wound swabs were shown to be positive for *Escherichia coli* and *Enterococcus faecium*. The empiric antibiotic therapy with imipenem and linezolid was therefore proven to be appropriate. One day later the patient suffered from a second septic hit due to perforation of the colon with the need for surgical colectomy and construction of a stump by Hartmann. *Escherichia coli* and *Enterococcus faecium* were again identified to be the dominant organisms in abdominal wound swabs. Moreover, *Morganella* sp. as well as *Candida* sp could be identified. Accordingly, a treatment with caspofungin was initiated for the next fourteen days. In contrast, the administration of imipenem and linezolid was stopped after seven days due to reconvalescence of the patient. However, three days afterwards the patient suffered from another septic hit due to an insufficiency of the stump by Hartmann. Accordingly, one further explorative laparotomy was performed and an intensive abdominal lavage was initiated. Abdominal wound swabs were shown to be positive for *Proteus vulgaris, Morganella* sp., *Escherichia coli, Enterococci* as well as *Bacteroides fragilis*. Accordingly, imipenem and linezolid were administered for another 12, respectively 10 days. In parallel, the patient revealed a reactivation of herpes simplex virus type 1 (HSV1) in tracheal secretions, so that the patient received acyclovir for fourteen days. In the further course of the septic disease the patient developed a fourth septic hit due to ventilator-associated pneumonia triggered by *Escherichia coli, Stenotrophomonas* as well *Klebsiella pneumoniae*. Antibiotic therapy was therefore stepwise switched to piperacillin/tazobactam, cotrimoxazole as well as ciprofloxacin. However, following a prolonged weaning phase the patient was then able to be transferred to the intermediate care ward after 3 months of ICU-treatment. Ultimately, the patient could be discharged from hospital another 2 weeks later. In this figure, the antibiotic treatment regime, SIQ scores for species identified via NGS and cfDNA concentrations of the respective plasma samples are plotted over the timeline of the trial period for patient S60. Pertinent (clinical microbiology) laboratory results are marked by arrows to the day the clinical specimen was obtained. The following abbreviations were used: blood culture (BC), central venous catheter (CVC), tracheal secretion (TS), bronchoalveolar lavage (BAL), herpes simplex virus 1 (HSV1), imipenem (IPM), linezolid (LZD), caspofungin (CFG), aciclovir (ACV), piperacillin tazobactam (TZP), cotrimoxazol (CTX), ceftazidime (CAZ). Antibacterial antibiotics were colored in light grey. The relative amount of bacteria found by conventional clinical microbiology is indicated with plenty (p), medium (m) or scarce (s). For a detailed list of anti-infectives abbreviations, see FIG. 18.

Figure 4:
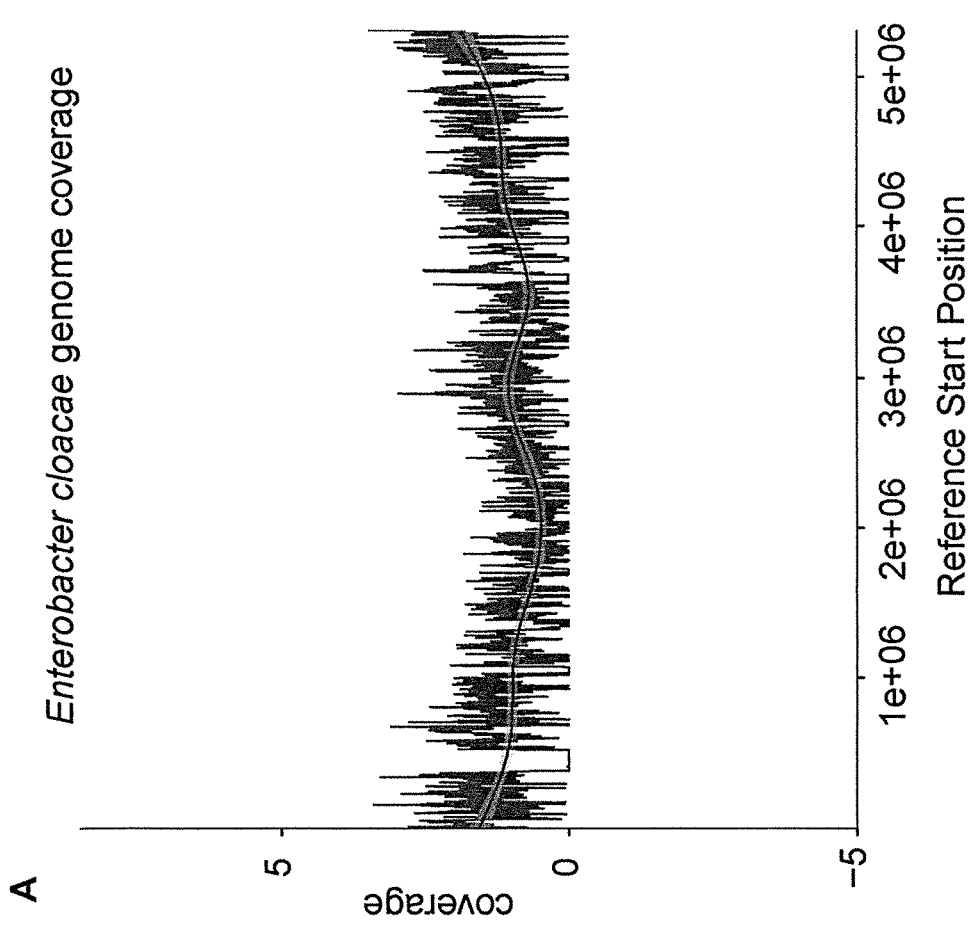

FIG. 4: shows Genome Coverage and resistance profile of *Enterobacter cloacae* in Patient S9 (A) Mean genome coverage of approximately 1 of the *E. cloacae* genome (5.2 MB). (B) Table with hits to the CARD database from all reads classified to *E. cloacae*. The CARD/Genbank accession number is listed, alias gene name, gene coverage calculated from read length ratio to gene length, number of reads mapped to this gene and the respective organism the sequence is assigned to. (C) Sequence alignment of the 3 reads mapped to mecA identified from the commercial plasma sample SX2. mecA corresponds to SEQ ID NO: 1. SX2_r1 corresponds to SEQ ID NO: SX2_r2 corresponds to SEQ ID NO: 3 and SX2_r3 corresponds to SEQ ID NO: 4.

FIG. 5: shows a schematic representation of the inventive process including process steps a) to e).

Figure 6:
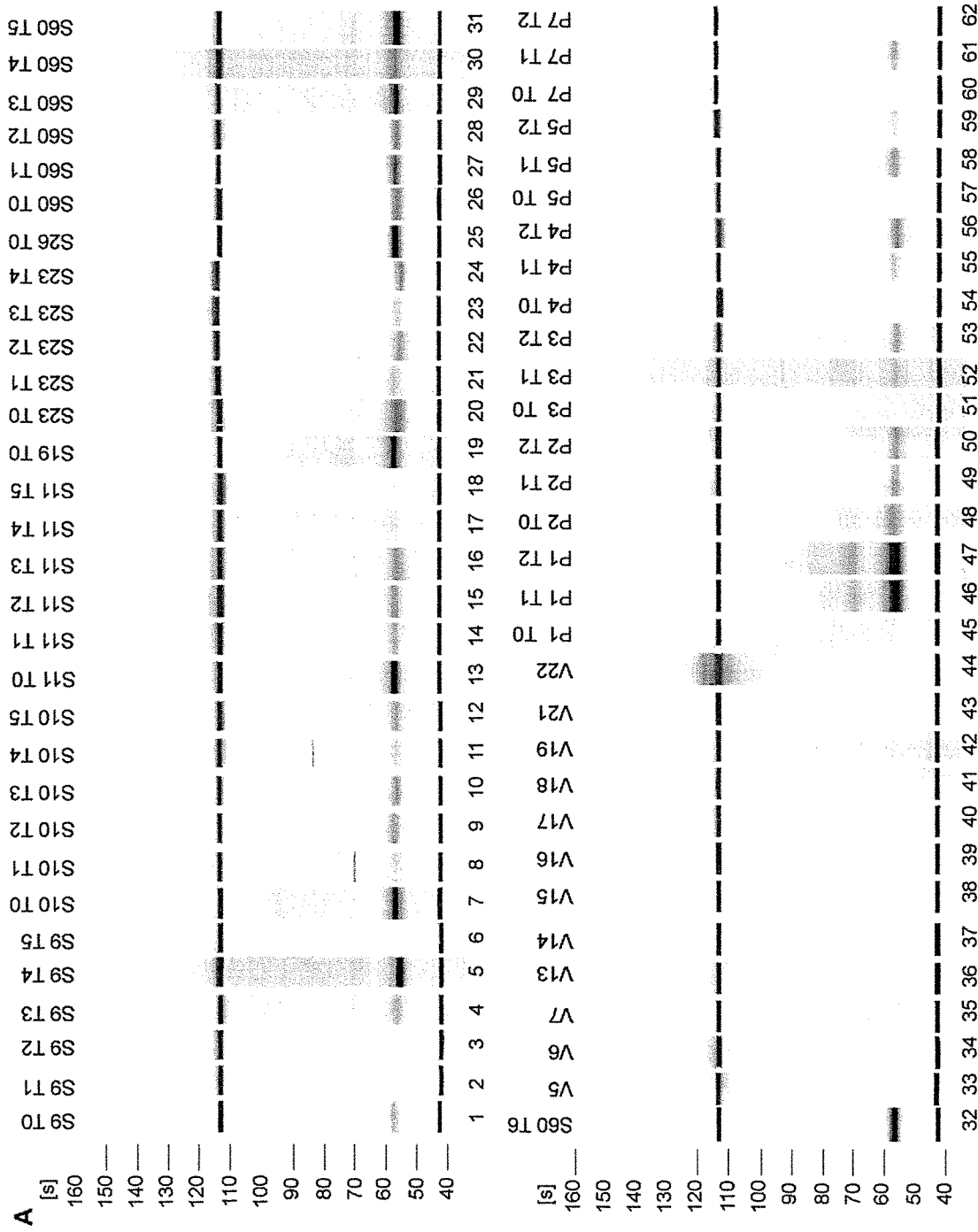
Figure 6:
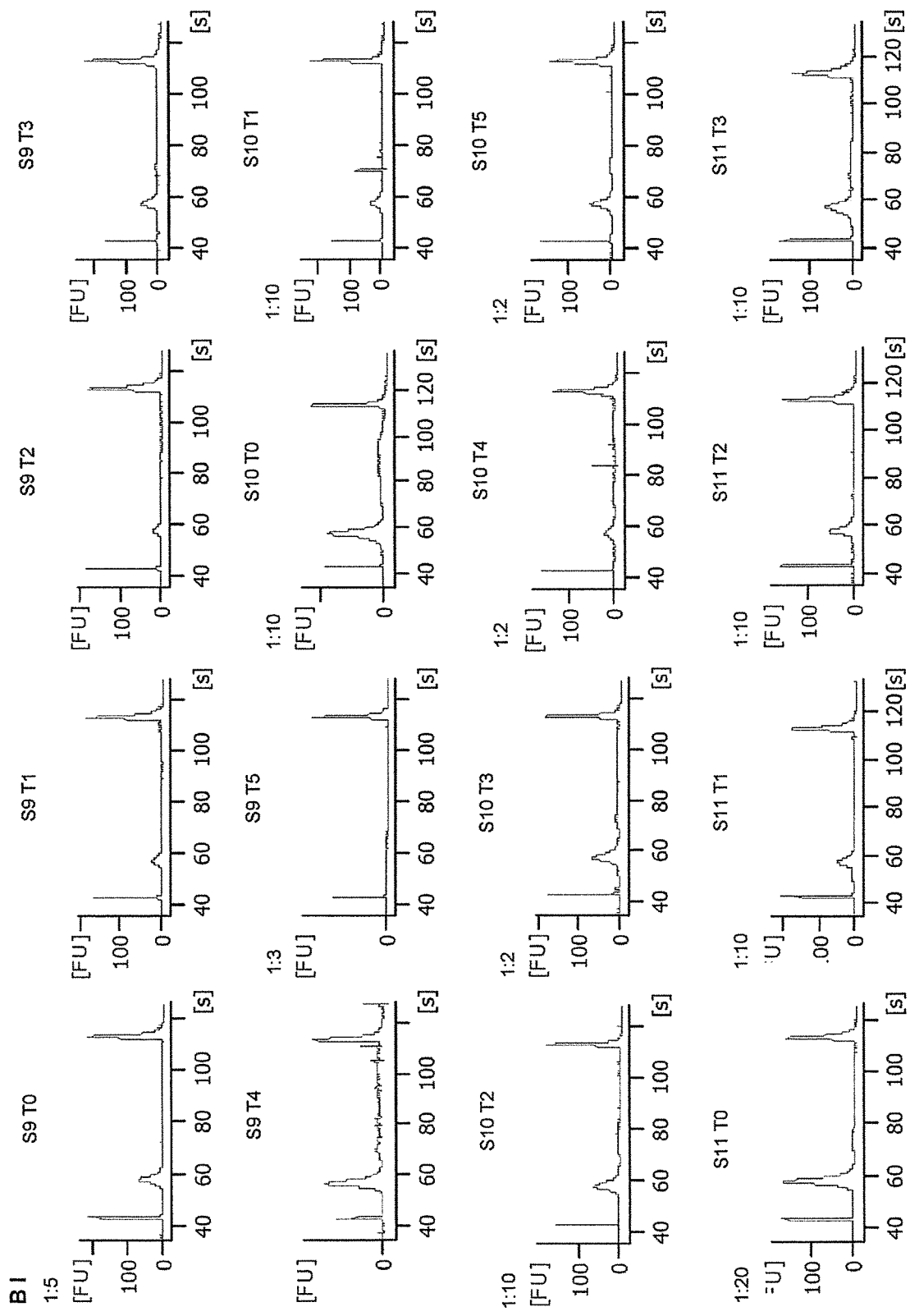
Figure 6:
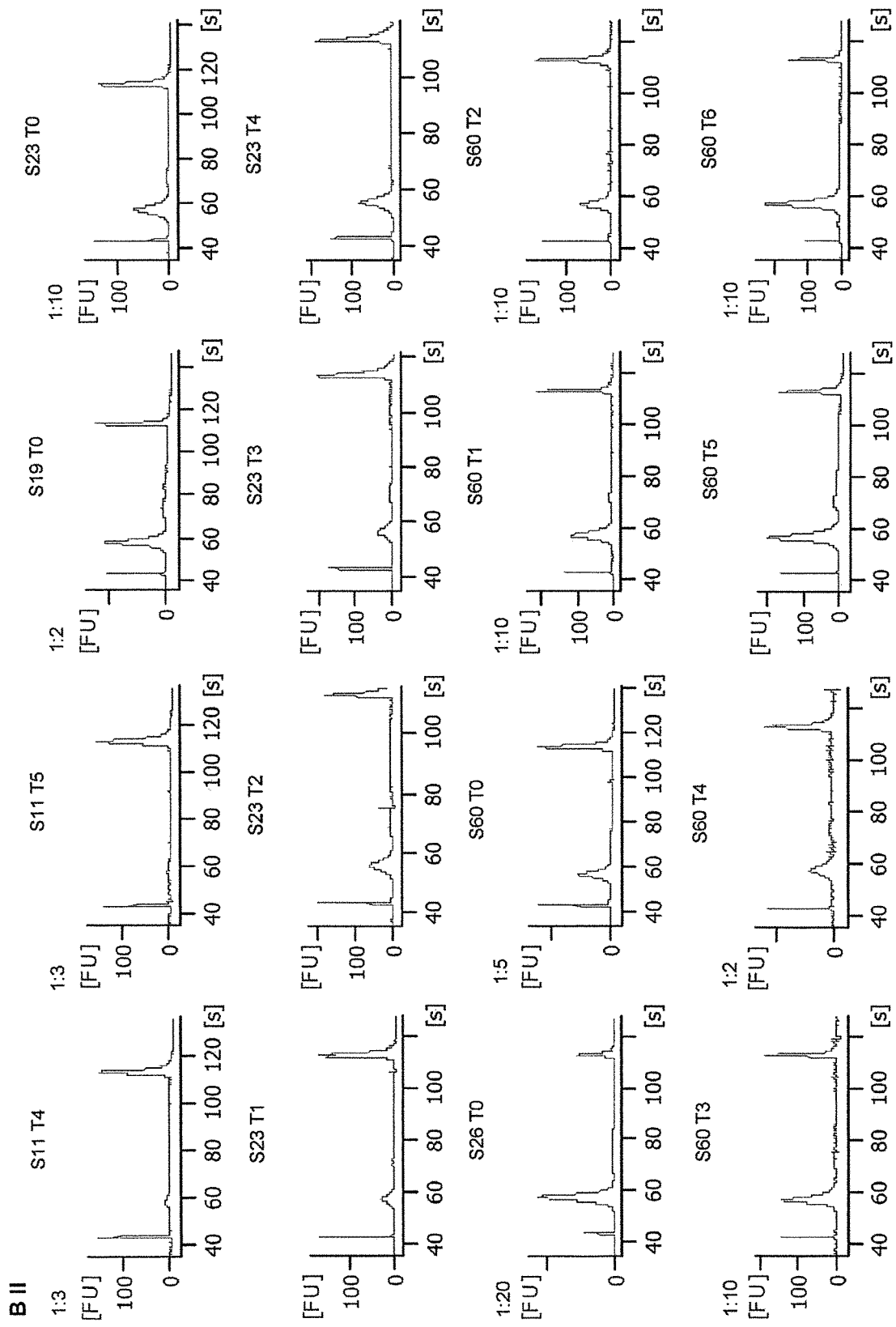
Figure 6:
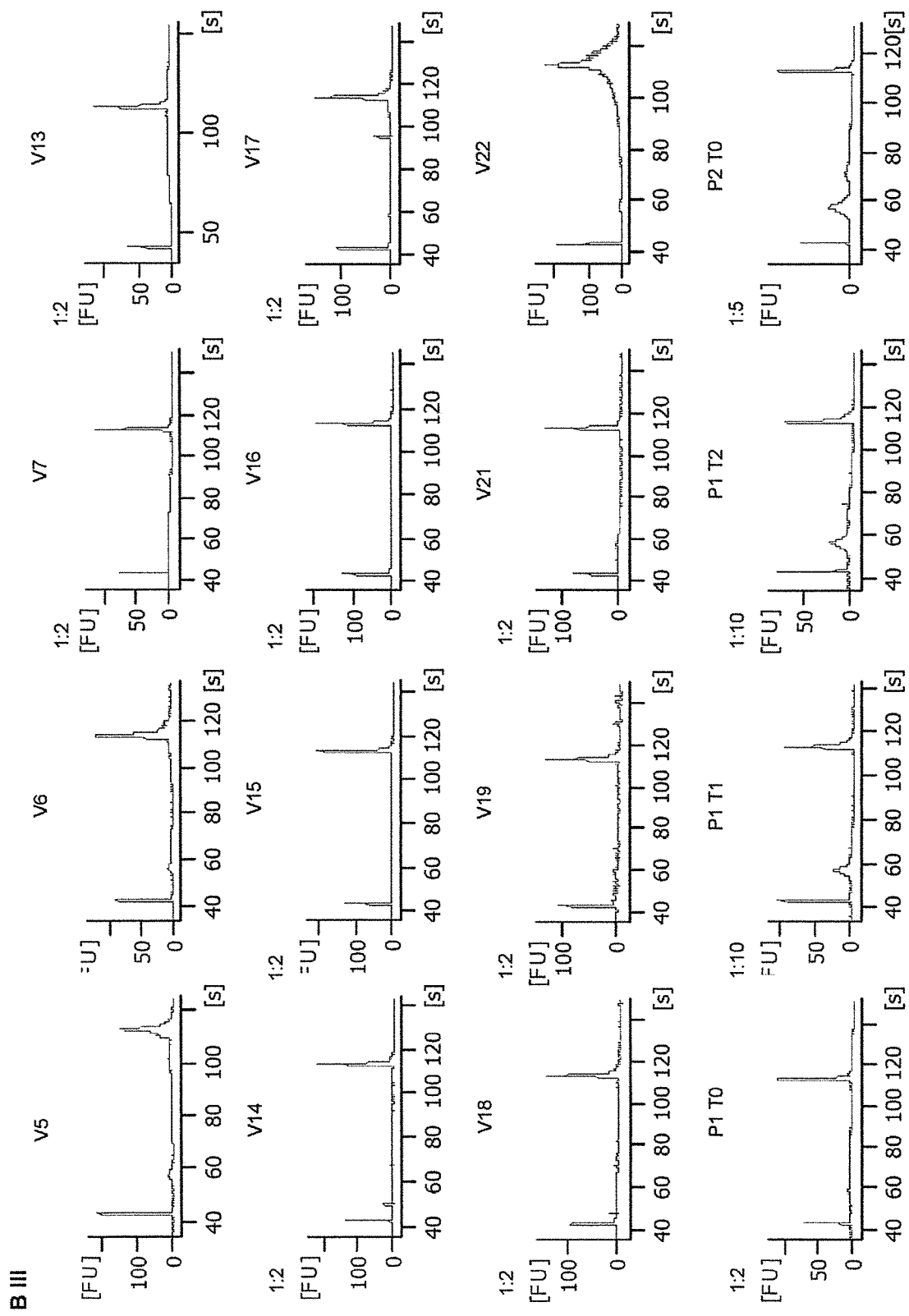

FIG. 6: Bioanalyzer profiles of cfDNA isolated from septic patients, non-infected (post-) surgery controls and healthy volunteers. (A) Gel-like visualization of the cfDNA profiles run on the Agilent Bioanalyzer with a High Sensitivity DNA chip. (B) Corresponding electropherograms, where the two outermost peaks are internal size standards.

Figure 7:
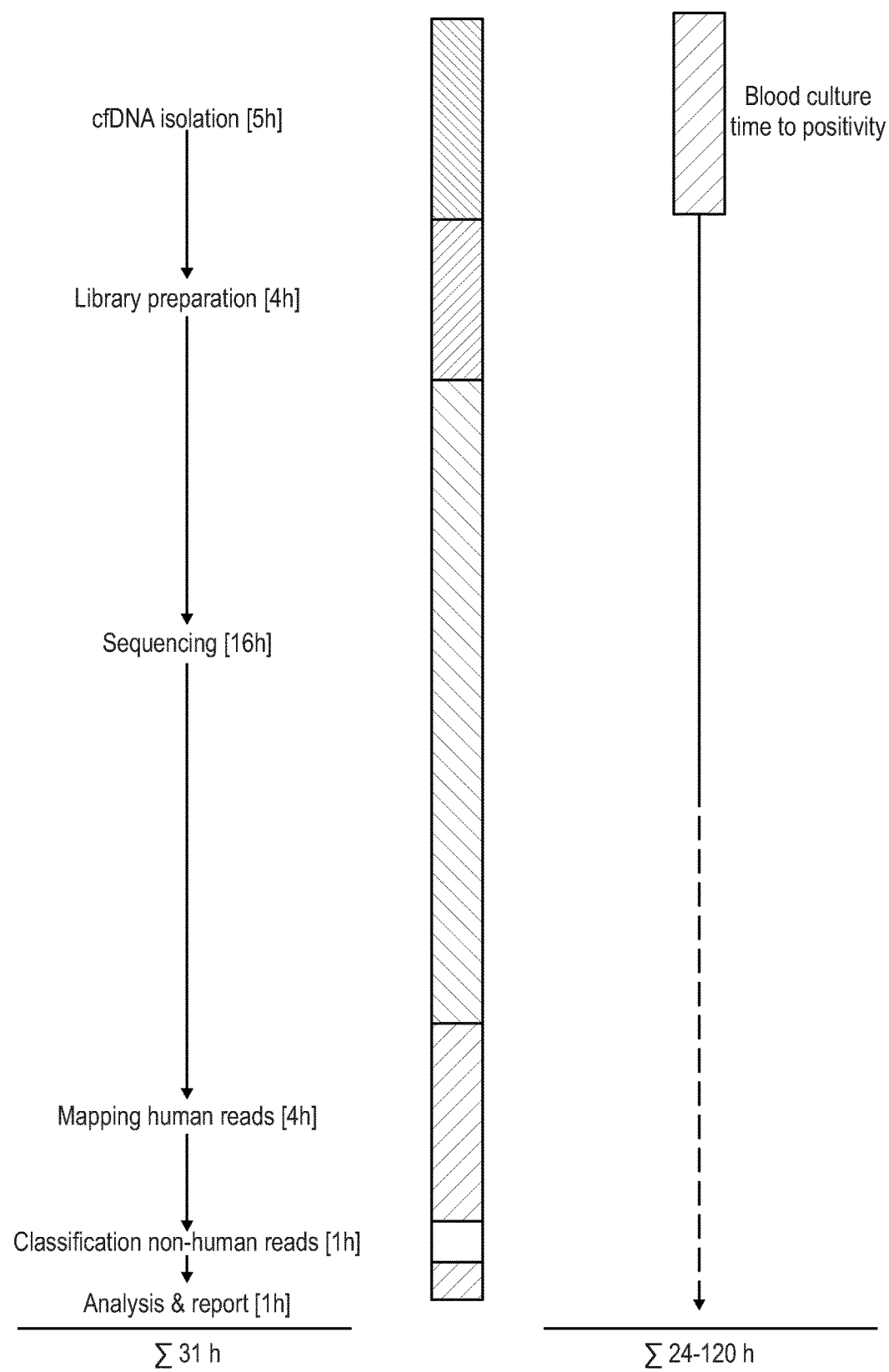

FIG. 7: Workflow and time distribution NGS-based pathogen identification and blood culture.

Flow chart and bar chart of the individual steps and the time required of the NGS-based identification of bacteremia-causing species and conventional blood culture. As time to positivity varies substantially, a time frame of 24 to 120 hours is given for blood culture.

FIG. 8: Distribution of species-specific normalized read counts in septic patients and controls for major pathogens in the sepsis setting. (closed: septic patients, open: controls (elective surgery (timepoint T0) and healthy volunteers).

Figure 9:
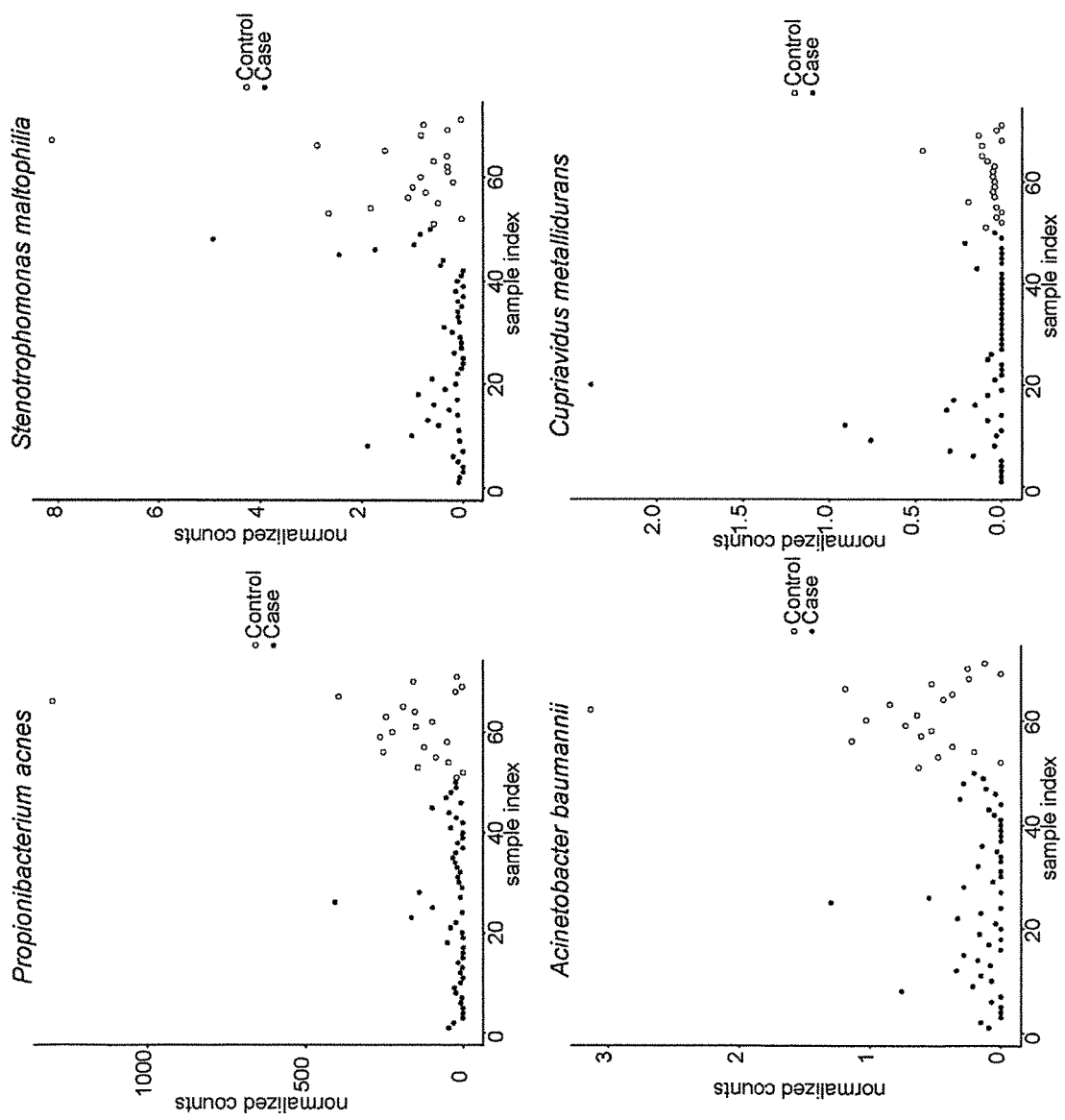

FIG. 9: Distribution of species-specific normalized read counts in septic patients and controls for potential contaminant species. (closed: septic patients, open: controls (elective surgery (timepoint T0) and healthy volunteers).

Figure 10:
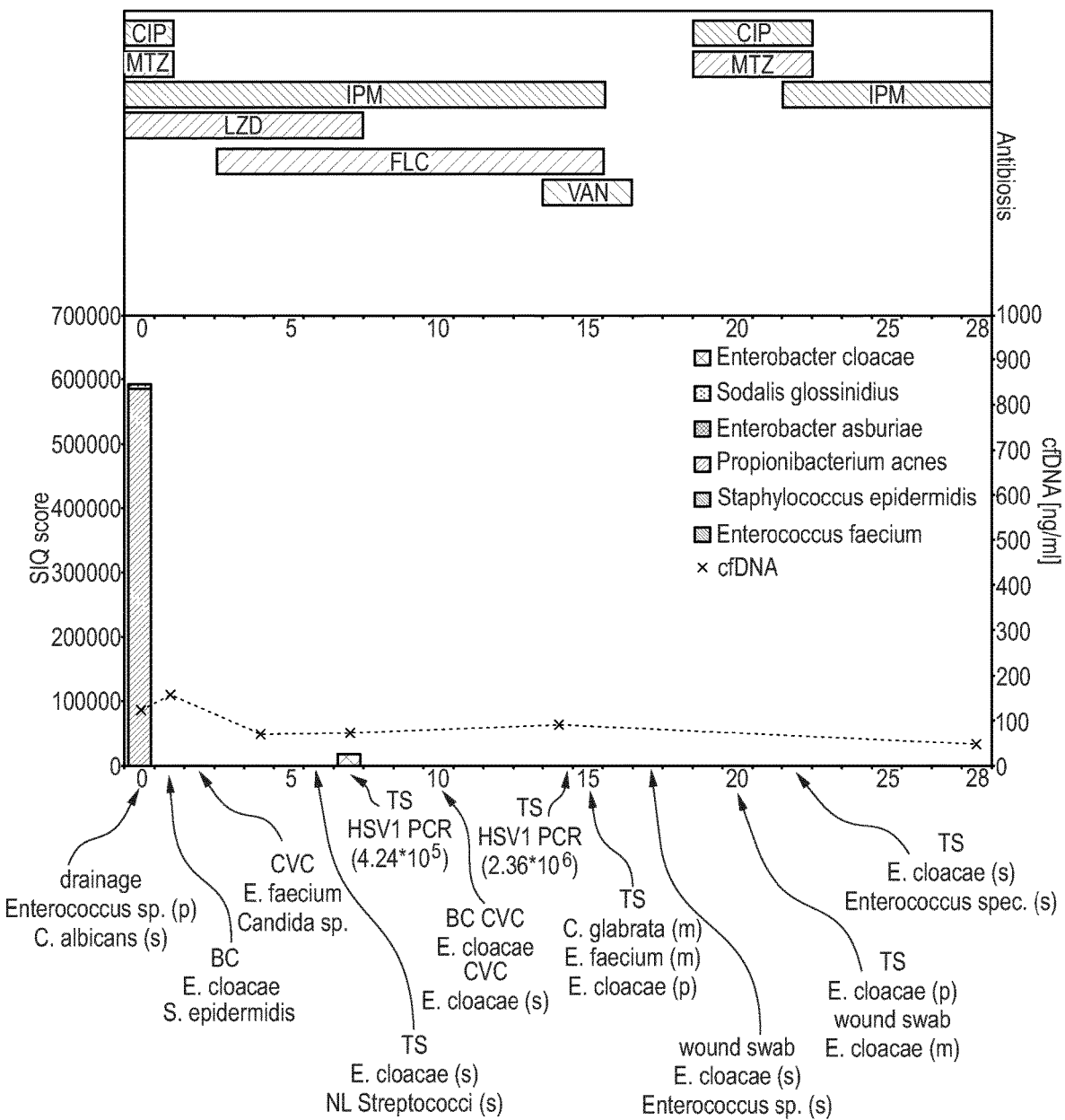

FIG. 10: Time course patient S9

A 82 year old male patient presented with a tumor of his bile duct with the need for an enlarged right-sided hemihepatectomy. Following surgical procedure the patient suffered from septic shock due to an ogilvie syndrome, so that a right sided hemicolectomie had to be performed. Septic shock was paralleled by repetitive positive blood cultures with *Enterobacter cloacae*. The more, *Enterobacter cloacae* was shown to be the cause for ventilator associated pneumonia one week after sepsis onset. Following antibiotic treatment, two different biotypes of *Enterobacter cloacae* could be observed, which both fulfilled the criteria of being multi drug resistant. The patient deceased 9 weeks after the onset of septic shock. In this figure, the antibiotic treatment regime, SIQ scores for species identified via NGS and cfDNA concentrations of the respective plasma samples are plotted over the timeline of the trial period for patient S9. Pertinent clinical microbiology laboratory results are marked by arrows at the day the clinical specimen was obtained. The following abbreviations were used: blood culture (BC), central venous catheter (CVC), tracheal secretion (TS), non-lysing (NL), ciproflocaxine (CIP), metronidazole (MTZ), imipenem (IPM), linezolid (LZD), fluconazole (FLC), vancomycin, (VAN), Anti-infectives are displayed as antibacterial antibiotics, antimycotics and antivirals in light grey, black and dark grey, respectively. The relative amount of bacteria found by conventional clinical microbiology is indicated with plenty (p), medium (m) or scarce (s). For a detailed list of anti-infectives abbreviations, see FIG. 18.

Figure 11:
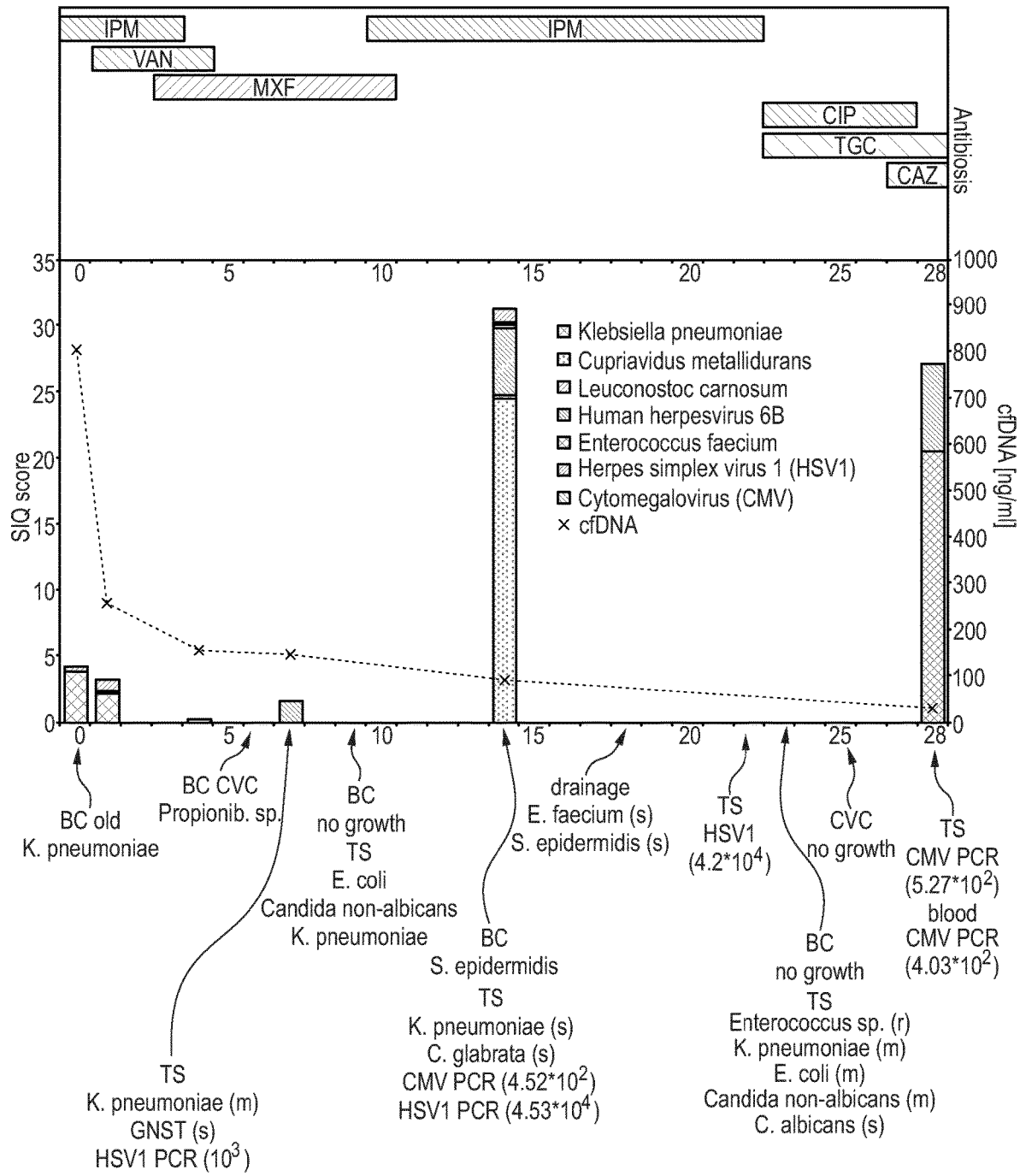

FIG. 11: Time course patient S11

A 62 year old male patient presented with a multilocular hepatocellular carcinoma with the need for a left-sided hemihepatectomy. Following the surgical procedure the patient suffered from septic shock due to severe pneumonia with *Klebsiella pneumoniae* as the dominant organism in blood cultures as well as tracheal secretions. Empiric antibiotic therapy was performed with imipenem, which was then switched to moxifloxacin based on the susceptibility findings. In the further course of the disease, *Klebsiella pneumoniae* was shown to be multi drug resistant. Although antibiotic therapy was adapted according to the findings of susceptibility testing, the pulmonary septic focus could not be removed sufficiently. In the end, the patient deceased by ongoing septic shock due to pneumonia with Klebsiella pneumonia two months after study inclusion. In addition, septic disease was shown to be accompanied by a reactivation of herpes simplex virus type 1 (HSV1) as well as cytomegalovirus (CMV) in different secretions as assessed by a PCR-based diagnostic procedure. These findings were in good agreement with NGS of plasma. In this figure, the antibiotic treatment regime, SIQ scores for species identified via NGS and cfDNA concentrations of the respective plasma samples are plotted over the timeline of the trial period for patient S11. Pertinent (clinical microbiology) laboratory results are marked by arrows to the day the clinical specimen was obtained. The following abbreviations were used: blood culture (BC), central venous catheter (CVC), tracheal secretion (TS), gram negative staphylococci (GNST), herpes simplex virus 1 (HSV1), imipenem (IPM), vancomycin, (VAN), moxiflocaxin (MXF), ciprofloxacin (CIP), tigecycline (TGC), ceftazidime (CAZ). Antibacterial antibiotics are displayed in light grey. The relative amount of bacteria found by conventional clinical microbiology is indicated with plenty (p), medium (m) or scarce (s). For a detailed list of anti-infectives abbreviations, see FIG. 18.

Figure 12:
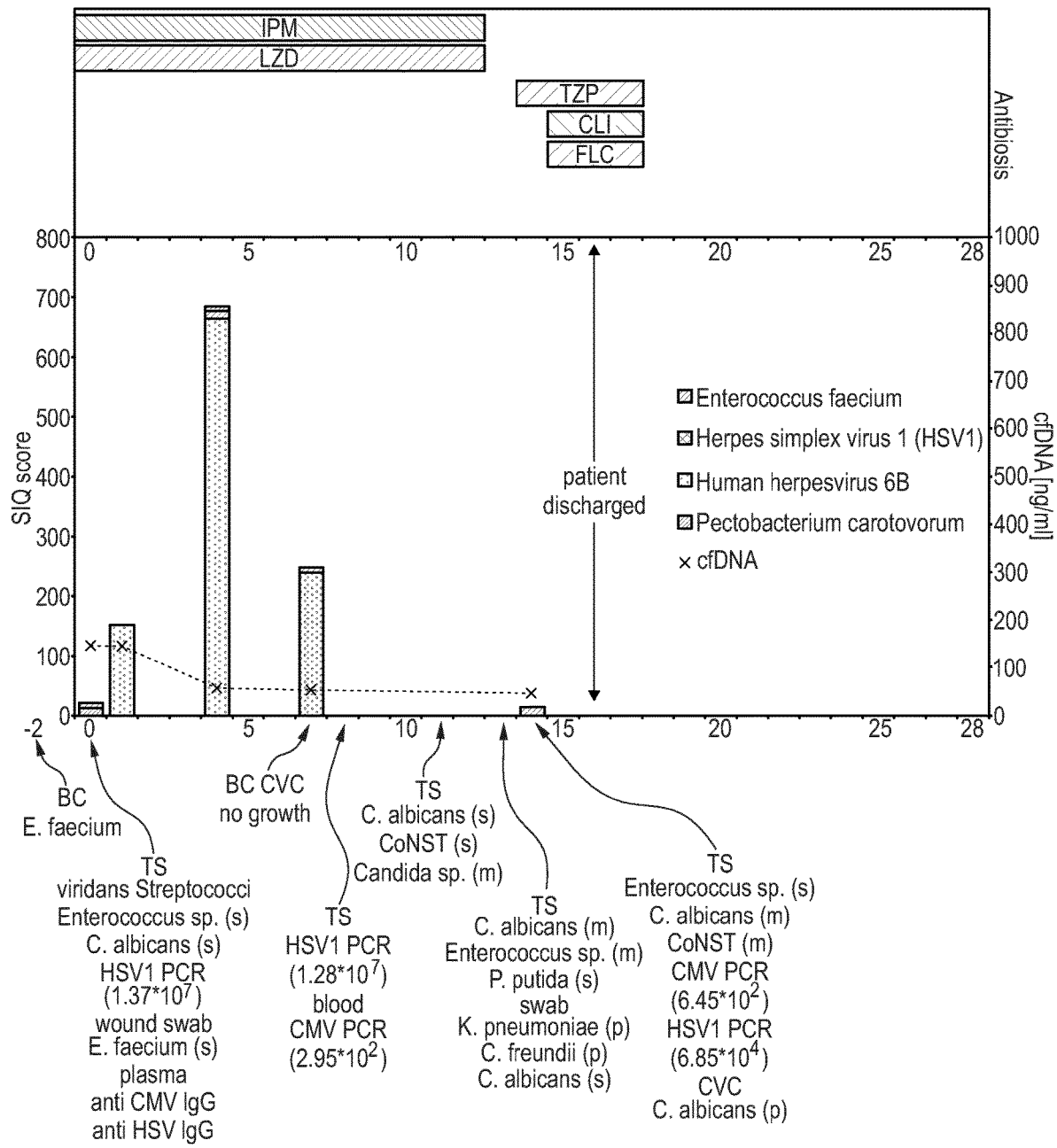

FIG. 12: Time course patient S23

A 77 year old male patient presented with septic shock due to an acute abdomen. An ischemic colitis with a perforation of the sigma and severe peritonitis was identified to be the septic focus, so that the patient underwent surgical colectomy. Abdominal wound swabs as well as the corresponding blood cultures were shown to be positive for *Enterococcus faecium* two days before inclusion in the study cohort. Empiric antibiotic therapy with imipenem and linezolid was therefore proven to be appropriate. In addition, this patient also revealed a reactivation of herpes simplex virus type 1 (HSV1) in tracheal secretions. These PCR-based findings could also be confirmed by NGS of plasma. Antibiotic treatment regime, SIQ scores for species identified via NGS and cfDNA concentrations of the respective plasma samples are plotted over the timeline of the trial period for patient S23. Pertinent (clinical microbiology) laboratory results are marked by arrows at the day the clinical specimen was obtained. The following abbreviations were used: blood culture (BC), tracheal secretion (TS), coagulase negative staphylococci (CoNST), imipeneme (IMP), linezolid (LZD), tazobactam (TZP), clindamycin (CLI), fluconazole (FLC). Anti-infectives are colored as antibacterial antibiotics and antimycotics in light grey and black, respectively. The relative amount of bacteria found by conventional clinical microbiology is indicated with plenty (p), medium (m) or scarce (s). For a detailed list of anti-infectives abbreviations, see FIG. 18.

Figure 13:
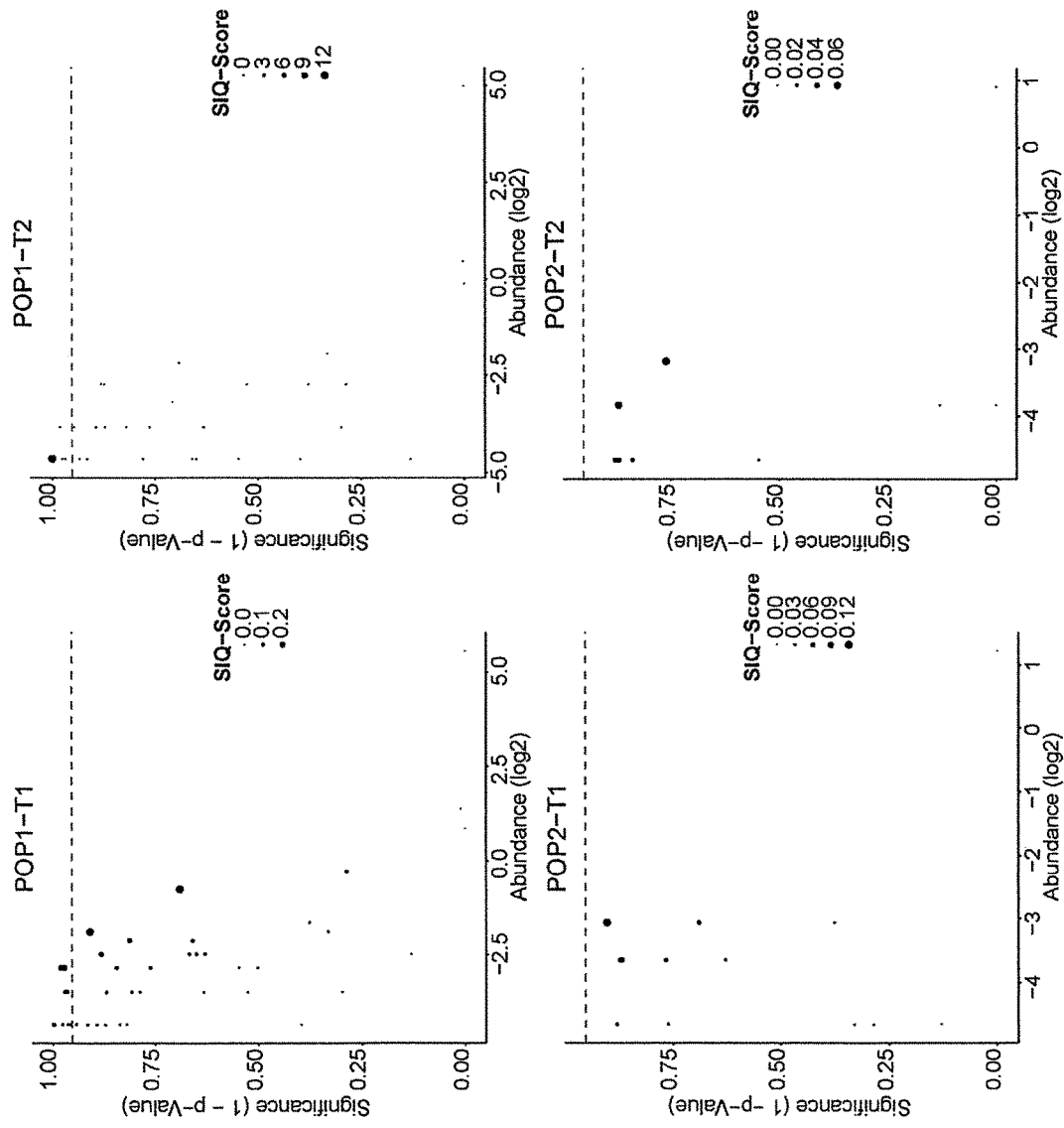

FIG. 13: SIQ plot for post-surgery patients P1-T1 and P2 T1

FIG. 14: Cohort statistics. In the present cohort, clear tendencies were discernible between the different subgroups. The lowest concentrations of cfDNA were obtained for the control group V, followed by the surgery group P T0. Higher concentrations were measured in group P following surgery (T1, T2) and in the septic group S, especially at the onset of sepsis. In group P the mean value was strongly increased by patient P2 (who interestingly also had elevated levels of PCT, CRP and IL-6 throughout all timepoints (data not shown)). The mean value of group P without Patient P2 was closer to the healthy volunteer group (P T0 without P2 mean 68.8 ng/ml), suggesting that the remaining discrepancy could be age-related. For six out of seven patients highest cfDNA concentrations were measured for the day of sepsis onset or 24 hours later. Five out of seven septic patients (S9, S10, S19, S23, S60) underwent major abdominal surgery within 2 days of sepsis onset, which likely contributed to elevated cfDNA concentrations. By comparison of classified reads between S T0 and P T0, it could be shown that for septic patients a significantly higher share of cfDNA could be assigned to microbial origin, suggesting a direct release of DNA from bacteria or co-release from phagocyting cells.

FIG. 15: List of fungal reference genomes included in the kraken database to identify microbial reads in non-human reads FIG. 16: Patient characteristics, sequencing statistics including normalized germ read counts and SIQ scores for the complete dataset FIG. 17: List of contaminant species identified from water controls FIG. 18: Anti-infectives abbreviations FIG. 19: List of organisms in human septic plasma pooled

EXAMPLES

Example 1

Human data result from a secondary analysis of a subset of patients participating in the RAMMSES-trial (German Clinical Trials Register: DRKS00000505). This observational clinical study was first approved by the local ethics committee (Trial-Code-Nr.: S123-2009) on 8 Jun. 2009. For the presented NGS procedures an amendment was submitted to the local ethics committee which was finally approved on 28 Nov. 2014.

The observational clinical study was conducted in the surgical intensive care unit of Heidelberg University Hospital, Germany. Study and control patients or their legal designees signed a written informed consent. In total, 120 patients in three groups were consecutively enrolled into the study from August 2009 to July 2010. The three groups included: (1.) 60 patients with septic shock, according to the criteria of the International Sepsis Definitions Conference [2], due to documented or suspected infection according to the criteria of the International Sepsis Forum Consensus Conference on Definitions of Infection in the Intensive Care Unit (ICU) [3], (2.) 30 postoperative controls following major abdominal surgery without any evidence of infection, and (3.) 30 healthy volunteers. Plasma samples from patients with septic shock were collected at sepsis onset (T0), and 24 hours (T1), 4 days (T2), 7 days (T3), 14 days (T4) and 28 days (T5) later. Plasma samples from the postoperative group were collected prior to surgery (T0), immediately following the end of the surgical procedure (T1) and 24 hours later (T2). Plasma samples from the volunteer group were collected once (T0).

For this secondary analysis, patients' electronic medical records were retrospectively screened for results from blood culture testing during septicemia. In Heidelberg University Hospital blood culture testing is routinely performed as described previously [4]: Whole blood samples are obtained via direct venipuncture, for example antecubital vein, applying sterile techniques and 10 mL blood is inoculated to an aerobic and anaerobic liquid culture medium, respectively (BACTEC PLUS, BD Biosciences, Heidelberg, Germany). Cultures are incubated for 5 days (BACTEC, BD Biosciences, Heidelberg, Germany), positive cultures are analyzed according to approved in-house hospital standard techniques including identification by VITEK2 (Biomerieux, Nuertingen, Germany) or MALDI TOF (Bruker, Madison, Wis., USA) and automated antimicrobial susceptibility testing (VITEK 2).

Quantification of HSV1 DNA and CMV DNA from plasma or tracheal secretion was performed via quantitative real time PCR as previously described [5]. Wound swabs and stool samples were cultivated as previously published [6,7].

Plasma was prepared from blood samples by centrifugation for 10 min at 292×g (1,200 rpm) and 4° C., snap frozen and stored at −80° C. until further processing. Nucleic acids were isolated from thawed plasma after a centrifugation step of 5 min at 1,000×g with the Circulating Nucleic Acid Kit (Qiagen) according to the manufacturer's protocol with the following exceptions: plasma volumes after centrifugation from 130 μl to 790 μl were adjusted to 1 ml with sterile phosphate buffered saline. Final elution of the nucleic acids from the spin column was carried out with 30 μl molecular biology grade water (5 Prime, Germany). The cfDNA was quantified with the Qubit dsDNA HS Assay Kit (Life Technologies) and quality was assessed with the High Sensitivity DNA kit on a Bioanalyzer (Agilent). Libraries for NGS were prepared from 1 ng cfDNA with the Nextera XT library preparation kit (Illumina), according to the manufacturer's protocol, with the exception that the final elution after bead clean-up was carried out in 34 μl of resuspension buffer (Illumina). Sequencing of the libraries was performed on a HiSeq2500 (Illumina) with a depth of 25-30 million 100 bp single end reads per sample. Since samples V6, V22 and P6 were initially sequenced with considerably more reads, those samples were randomly reduced in silico to 30 million representative subsampled reads.

Reads were cleaned from potential adapter contaminations, quality controlled and if necessary trimmed using BBDuk [sourceforge.net/project/bbmap/]. To pass the quality filter the read quality needs to surpass a Phred score of 20 and achieve a minimal length of 50 bp after trimming of low quality and adapter bases. Subsequently, NextGenMap [8] aligned quality controlled reads to the human reference genome [hg19] requiring a minimal identity between read and reference genome of 80%. Reads mapping to the human reference genome were excluded from further analysis. Because mapping algorithms cannot reliably map reads containing low complexity regions, including di- or trinucleotide repeats to the human genome [9], corresponding reads were removed. The exclusion of low complexity reads reduced false positive classifications during downstream analysis. Finally, for reads passing the complexity filtering, Kraken [10] assigned their systematic position using RefSeq release (version 68) comprising 35,749 bacterial and 4,340 viral genomes complemented by twelve selected fungal genomes (FIG. 15) as reference database. This leads to a distribution of classified reads from a sample to the nodes of the taxonomic tree. In other words the reads identify bacterial/fungal/viral clades. However, since several Xanthomonas species are described as contaminants of all samples, all of them as well as the Illumina sequencing spike-in PhiX [11] were excluded.

To quantitatively compare the number of reads that map to different microbial taxonomic classifications between different samples, the read-count were normalized by the library size of the sample. The remaining read counts for each identified species were then further analyzed by an n×(s+1) dimensional count matrix D, where n is the number of control samples and s the number of all species detected in all samples. Thus, $D_{ij}$ defines the number of reads found in control sample i for species j. $D_{i(s+1)}$ defines the number of reads which cannot be assigned to any species.

Since the number of reads for one species is typically low, it is safe to assume that the read counts for species j (j=1, . . . , s) are Poisson distributed with parameter $$\lambda_j = \frac{\sum_{k=i}^{n} D_{k,j}}{n}. \tag{1}$$

To test this assumption for each species a standard $\chi^2$ goodness of fit test is performed.

For reads sequenced from patient plasma, the same data processing pipeline is applied, that yields a read count vector $C=(C_1, \ldots, C_s, C_{s+1})$. Based on the Poisson distribution with species-specific parameter $\lambda_j$ the p-value to observe at least $C_j$ read counts in a patient sample is computed as $$P(X \geq C_j | \lambda_j) = \sum_{k \geq C_j} \frac{e^{-\lambda_j} \lambda_j^k}{k!}. \tag{2}$$

The p-value is directly dependent on the size of the null distribution (i.e. the number of control samples). If the p-value is small, then one would reject the hypothesis that the read count of species j in the patient sample follows the Poisson distribution derived from the healthy individuals and one would conclude that the respective species occurs too often in the patient.

To allow for a different interpretation and visualization of the results for all species found in a patient sample, the SIQ score (Sepsis Indicating Quantifier) for species j is introduced as $$SIQ_j = C_j^* - (\log_{10}(P(X \geq C_j | \lambda_j))) \tag{3}$$

In order to identify possible resistance genes, reads classified to the most probable infectious agent (*Enterobacter cloacae*) in patient S9 were mapped against the downloaded CARD resistance gene database [12] using NextGenMap with the following parameters: Sensitivity (-s), minimal identity (-i) and minimal number of mapped residues (-R) of 0.9.

Results

Elevated levels of cfDNA in septic patients reveal microbial DNA fragments

In order to test the diagnostic potential of cfDNA to identify infecting microorganisms in septic patients, in total 62 plasma samples were analyzed in this study. The septic group (S, n=7) comprised one (T0) to six (T6) plasma specimens starting at the onset of sepsis (32 samples). Healthy volunteers and patients undergoing major abdominal surgery served as uninfected controls. Healthy volunteers (V; n=12) provided one plasma sample (T0), patients of the postoperative control group (P; n=6) contributed three plasma specimens (T0-T2). Mean ages were 70.5 years, 26.4 years and 64.2 years of groups S, V and P, respectively (FIG. 14).

FIG. 14: Patient characteristics, cfDNA concentration and sequencing statistics.

Patients were grouped as septic patients (S), healthy volunteers (V) and non-infected patients following major abdominal surgery (P). Of the total reads (sequencing depth), all reads mapped to human reference genome hg19 are classified as human reads, the remaining reads are denoted as unmapped. The proportion of unmapped reads classified to any species using Kraken are specified here as classified.

Septic patients were monitored by a comprehensive clinical microbiology workup, which included regular blood cultures, cultivation of other secretions or catheter tips, swabs, and if indicated tests for fungi and viruses. Five out of seven patients survived the 28 day trial period. Patients and controls were initially recruited for evaluation of methylglyoxal as biomarker for septic shock [1] and the trial was subsequently amended for NGS based diagnosis. cfDNA isolation from patient and control plasma revealed a characteristic, predominantly apoptosis-associated size pattern [13,14], expected for nucleosomal DNA (FIG. 6). Following cfDNA isolation, the concentration of eluted DNA was calculated as a function of the input plasma volume and normalized to 1 ml. Concentrations of cfDNA were significantly increased in patients with septic shock (mean S 197.23 ng/ml), especially at the onset of sepsis (mean S T0 377.30 ng/ml) (FIG. 1).

Elevated concentrations were also measured in plasma of post-surgery patients (P T1-T2 mean 451.63 ng/ml) compared to uninfected controls before surgery and healthy volunteers (P T0 mean 149.33 ng/ml; V mean 55.43 ng/ml). From isolated cfDNA, sequencing libraries were prepared and analyzed by Illumina high throughput sequencing with 100 bp length and a mean coverage of approximately 26 million reads. Using the workflow as per the present invention to quantitatively identify non-human nucleic acids in patient plasma (FIG. 7), the total turnaround time starting from plasma is approximately 30 hours, where the most time-consuming step is sequencing, which was accomplished in rapid run mode on a HiSeq2500 within 16 hours. This is highly competitive to standard blood culture with a time to positivity of 24-120 hours. In automated systems, blood cultures are routinely incubated for five days [17].

FIG. 14 summarizes the sequencing statistics for human reads, unmapped reads and the classified proportion of unmapped reads. Despite the variation in cfDNA concentration over all compared groups the average proportion of human reads were similar (96.36%, 96.52% and 96.21% in groups S T0, V and P T0, respectively), correspondingly the unmapped proportion of reads. The average classified reads were higher in septic patients at the onset of sepsis (9.82%, 3.50% and 2.64% in groups S T0, V and P T0). Over all longitudinal samples of each group, this effect decreased (human reads: 97.79%, 96.52% and 97.22%; classified reads: 4.24%, 3.50% and 2.31% in groups S, V and P, respectively). In post-surgery controls (T1 and T2) elevated amounts of cfDNA (451.63 ng/ml) were linked to the highest proportion of human reads (97.72%) and lowest proportion of non-human classified reads (2.14%). However it should be noted that the proportion of classified reads includes contaminant PhiX reads and reads classified to *Xanthomonas campestris*, which were discarded as contaminants in downstream analysis.

Following normalization to library size, classified reads were used to diagnose the causative pathogen based on the microbial cfDNA fraction of septic patients compared to non-infected controls.

Establishment of a significance indicating quantifier (SIQ) as a quantitative score for pathogen calling The principle for quantitative assessment of microbial reads for a patient in comparison to uninfected controls is illustrated in FIG. 2 A. The principle is further exemplified with data from one patient (FIG. 2B-2E). From each plasma sample normalized read counts of classified non-human reads were calculated which results in the classification of several species. In case of patient S9 with positive blood cultures for *E. cloacae* at the onset of sepsis, distinctly higher abundant *Enterobacter cloacae* reads were found compared to a set of species with very low abundance normalized reads (FIG. 2B). To evaluate the significance of read abundances for all species classified, normalized read counts were compared for each species between all septic patients and controls. The abundance of normalized reads for *E. cloacae* in patients and controls was evenly distributed close to zero except for timepoint T0 of patient S9 (1,907.33, FIG. 2C). In contrast, normalized read counts for a common skin commensal like *Propionibacterium* acnes were randomly distributed over all samples and higher abundances were especially detected in samples obtained from uninfected controls (FIG. 2D). This effect was observed for a number of possible ubiquitous contaminant species (FIG. 17). A purely quantitative approach to count microbe-derived nucleic acid fragments is therefore misleading and a major pitfall in current molecular diagnostic approaches. To aid in clinical decisions, therefore abundance and unlikeliness of observed read counts for each species found in a sample in a coherent visualization were combined. The log 2 ratio of normalized reads is plotted on the x-axis, whereas 1-p-value is plotted on the y-axis (FIG. 2E). Species which are significantly represented in a sample with a p-value <0.05 compared to controls are considered significant (FIG. 2E). To further discriminate among these species, the individual SIQ score is represented by the radius of the datapoint. The species with highest abundance and significance found in cfDNA of patient S9 at the onset of sepsis is therefore *Enterobacter cloacae* with a SIQ score of 5,000. This further implicates that species with high read counts will receive a low SIQ score if ubiquitously present in all other samples and controls. In contrast, species with very few reads but low prevalence will receive a high SIQ score. This principle helps highlighting low abundant but significant pathogen-associated reads from high abundant low significant contaminant reads.

Clinical Relevance of the SIQ Score

The SIQ score permits an absolute comparison between different microbial species found in one sample. Accordingly, besides the data-driven identification of pathogens in clinical specimens this method can be highly useful in monitoring a patient's bacterial load and response to targeted treatment and complement standard clinical microbiology. To assess the relevance of the SIQ score in clinical diagnostics, sequencing results were compared with clinical microbiology data, supplemented with anti-infective therapy over the trial period of 28 days. Data were compiled for all patients with more than two plasma collections (five out of seven patients, FIG. 10-12) and is shown for patients S10 and S60 in FIG. 3. Patient S10 (FIG. 3A) developed septic shock due to severe pneumonia, following a gastrectomy to remove a tumor of his stomach. On study enrollment, the first blood culture and subsequent samples from other secretions were positive for *Staphylococcus aureus*. Apart from *S. aureus*, in earlier respiratory specimens also significant viral burden (herpes simplex virus 1 (HSV1), $9.87 \times 10^6$ copies/ml) and low fungal burden (*Candida albicans*) were detected by qPCR or cultivation, respectively. Cultivation of blood from later samplings were negative, however blood culture drawn from the central venous catheter (BC CVC) yielded positive cultures for *Enterococcus faecium* and *S. epidermidis*, suggesting possible contamination common to blood cultures drawn from intravascular lines [18]. Sequencing of plasma samples confirmed *S. aureus* as the predominant organism in the patient's blood at all observed timepoints with SIQ scores of 125.24, 720.41, 12.86, 2 and 0.03. The highest SIQ score for *S. aureus* was observed on day 1 after sepsis onset, and strongly declined afterwards. On day 7 the highest SIQ score was obtained for HSV1 (43.07). HSV1 was also detected by qPCR on day 14 in tracheal secretion ($8.5 \times 10^5$ copies/ml) but otherwise in no other sample (qPCR or NGS). Minor NGS findings were *Pectobacterium carotovorum* and *Staphylococcus epidermidis*. Although the genome sequence was manually included in the database, *C. albicans* was not detected in plasma samples by NGS. Equally, no reads were obtained for *E. faecium*. According to *S. aureus* being the clinically relevant organism and its susceptibility to methicillin, the patient was treated with flucloxacillin, whereas reactivated HSV1 was treated with aciclovir. The patient was discharged to normal ward six weeks after the onset of septic shock. Regarding cfDNA plasma concentrations, a stepwise reduction from initially elevated levels with a strong dip at day one could be observed for this patient. A similar course of gradual decline in cfDNA concentrations could be observed for other patients with the exception of patient S60, where the highest concentration in cfDNA was observed for day 28 (FIG. 3B). Patient S60 suffered from recurring episodes of bowel leakage accompanied by several septic hits and underwent repetitive reconstructive abdominal surgery. Interestingly, in the course of the sepsis, no positive blood culture could be obtained for this patient, with the exception of a single bottle positive for *Staphylococcus epidermidis* one day before study inclusion. Initial empiric antibiotic therapy with imipenem and linezolid was continued due to confirmative results of abdominal wound swabs positive for *Escherichia coli* and *Enterococcus faecium*. Later samplings including intraabdominal lavage and further wound swabs (obtained on day 7, 11, 14 and 21) were continuously positive for *E. coli* (and partially Enterococci). Additionally, Proteus (vulgaris), *C. albicans* and *Morganella* (*morganii*) were detected. Tracheal secretions were furthermore tested positive for HSV1 and/or *C. albicans*. In the further course of infection, the patient developed a ventilator-associated pneumonia due to *E. coli, Stenotrophomonas* and *Klebsiella pneumoniae*. NGS-based results of the cfDNA of this patient's plasma were concordant with clinical microbiology results over the complete timecourse. Samples acquired in the earlier septic phase (day 0, 1, 4, 7, 14 and 21) confirmed the clinical representation of polymicrobial abdominal infection due to *E. coli, E. faecium* and *Bacteroides fragilis*. Only limited read counts were obtained for plasma of day 1, still *E. coli* and *B. fragilis* were found to be the species with the highest SIQ scores. From day 4 to 14, elevated amounts of *C. albicans* cfDNA were measured (SIQ scores 8.17, 1.97 and 290.53 for days 4, 7 and 14). Furthermore, results from quantitative PCR of HSV1 from tracheal secretions could also be confirmed by NGS (day 7). Although bacteria of the genus *Morganella* were detected as early as day 1 via cultivation, reads classified to *Morganella morganii* were only detected in plasma obtained on day 21. Lastly, the deterioration of the patient towards a ventilator-associated pneumonia at the end of the study period was equally confirmed by sequencing results with SIQ scores of 1341.37 for *K. pneumonia* and 68.58 for *Bacteroides fragilis* in plasma obtained on day 28. However, no elevated levels of *Stenotrophomonas* DNA were observed from plasma specimens. cfDNA levels of this patient were elevated on day 2, 7 and highest on day 28. The patient could be transferred to intermediate care after 3 months of ICU treatment and was ultimately discharged another 2 weeks later.

For seven out of seven patients positive blood cultures were received. However, in one patient (S60), contamination of blood culture seemed likely [19], as the cultivated bacterium was *S. epidermidis* from only one culture bottle (FIG. 3B). Furthermore, three out of seven patients already obtained a positive culture before inclusion in the study and six out of seven already received anti-infective therapy before onset of sepsis. With NGS, convincing results for all patients that matched the findings of blood culture in six out of seven cases (except for S60) were obtained. Furthermore, the SIQ results obtained for patient S60 at sepsis onset (polymicrobial infection with *E. coli, E. faecium* and *B. fragilis*) are concordant with the intra-abdominal swabs obtained during abdominal surgery and the clinical course of sepsis caused by bowel leakage, suggesting a superior sensitivity of the procedure as per the present invention compared to standard blood culture. Intriguingly, NGS results from plasma samples also matched data from other specimens such as tracheal secretion, swabs or catheter cultivation for all patients analyzed (FIG. 10-12).

Species-Specific Reads Could be Assigned to Resistance Genes

Analysis of patient S9 revealed a high amount of reads (58,460 raw reads) that could be uniquely assigned to the causative pathogen *E. cloacae*. Consequently, the respective genome shows an evenly distributed coverage of approximately one (FIG. 4A). This could be leveraged such that intrinsically resistance associated genes should be detectable in this case. Mapping the respective reads against the CARD database with no mismatch resulted in only few hits with gene coverages between 0.02-0.6 (FIG. 4B). Here, the identified genes contained several variants of RNA polymerase subunit B (rpoB) and the transcriptional regulator RobA, which are part of the database as potential antibiotic resistance genes but do not comprise antibiotic resistance per se.

Furthermore, a purchased pooled plasma sample (Seralab) of five donors suffering from sepsis was analyzed. Three of the five donors were diagnosed with *S. aureus* as the underlying pathogen, one with *Bacillus* non-anthracis and one patient was diagnosed with *viridans streptococci* (FIG. 19). Reads classified to *S. aureus*, but not to the other genera mentioned, were identified in NGS data. The sample with a higher coverage of 330 Mio reads was sequenced, wherein 2150 reads of *S. aureus* were identified. Searching for resistance genes by mapping against the CARD database identified 3 hits to mecA, among others.

The material in the ASCII text file, named GLEISS1-58853-Corrected-Sequence-Listing2, created Jun. 7, 2018, file size of 1.931 kbytes, is hereby incorporated by reference.

REFERENCES

1. Brenner T, Fleming T, Uhle F, Silaff S, Schmitt F, Salgado E, Ulrich A, Zimmermann S, Bruckner T, Martin E et al: Methylglyoxal as a new biomarker in patients with septic shock: an observational clinical study. *Crit Care* 2014, 18(6):683.
2. Levy M M, Fink M P, Marshall J C, Abraham E, Angus D, Cook D, Cohen J, Opal S M, Vincent J L, Ramsay G: 2001 SCCM/ESICM/ACCP/ATS/SIS International Sepsis Definitions Conference. *Crit Care Med* 2003, 31(4): 1250-1256.
3. Calandra T, Cohen J: The international sepsis forum consensus conference on definitions of infection in the intensive care unit. *Crit Care Med* 2005, 33(7):1538-1548.
4. Gumbinger C, Hug A, Murle B, Berger B, Zorn M, Becker K P, Zimmermann S, Dalpke A H, Veltkamp R: Early blood-based microbiological testing is ineffective in severe stroke patients. *J Neurol Sci,* 325(1-2):46-50.
5. Brenner T, Rosenhagen C, Hornig I, Schmidt K, Lichtenstern C, Mieth M, Bruckner T, Martin E, Schnitzler P, Hofer S et al: Viral infections in septic shock (VISS-trial)-crosslinks between inflammation and immunosuppression. *J Surg Res* 2012, 176(2):571-582.
6. Mischnik A, Mieth M, Busch C J, Hofer S, Zimmermann S: First evaluation of automated specimen inoculation for wound swab samples by use of the Previ Isola system compared to manual inoculation in a routine laboratory: finding a cost-effective and accurate approach. *J Clin Microbiol* 2012, 50(8):2732-2736.
7. Mischnik A, Trampe M, Zimmermann S: Evaluation of the impact of automated specimen inoculation, using Previ Isola, on the quality of and technical time for stool cultures. *Ann Lab Med* 2015, 35(1):82-88.
8. Sedlazeck F J, Rescheneder P, von Haeseler A: NextGenMap: fast and accurate read mapping in highly polymorphic genomes. *Bioinformatics* 2013, 29(21):2790-2791.
9. Horie M, Honda T, Suzuki Y, Kobayashi Y, Daito T, Oshida T, Ikuta K, Jern P, Gojobori T, Coffin J M et al: Endogenous non-retroviral RNA virus elements in mammalian genomes. *Nature* 2010, 463(7277):84-87.
10. Wood D E, Salzberg S L: Kraken: ultrafast metagenomic sequence classification using exact alignments. *Genome biology* 2014, 15(3):R46.
11. Susannah J Salter M J C, Elena M Turek, Szymon T Calus, William O Cookson, Miriam F Moffatt, Paul Turner J P, Nicholas J Loman and Alan W Walker: Reagent and laboratory contamination can critically impact sequence-based microbiome analyses. *BMC Biology* 2014, 12:87.
12. McArthur A G, Waglechner N, Nizam F, Yan A, Azad M A, Baylay A J, Bhullar K, Canova M J, De Pascale G, Ejim L et al: The comprehensive antibiotic resistance database. *Antimicrobial agents and chemotherapy* 2013, 57(7):3348-3357.
13. Giacona M B, Ruben G C, Iczkowski K A, Roos T B, Porter D M, Sorenson GD: Cell-free DNA in human blood plasma: length measurements in patients with pancreatic cancer and healthy controls. *Pancreas* 1998, 17(1):89-97.
14. Lichtenstein A V, Melkonyan H S, Tomei L D, Umansky S R: Circulating nucleic acids and apoptosis. *Ann N Y Acad Sci* 2001, 945:239-249.
15. Martins G A, Kawamura M T, Carvalho Mda G: Detection of DNA in the plasma of septic patients. *Ann N Y Acad Sci* 2000, 906:134-140.
16. Zeerleder S, Zwart B, Wuillemin W A, Aarden L A, Groeneveld A B, Caliezi C, van Nieuwenhuijze A E, van Mierlo G J, Eerenberg A J, Lammle B et al: Elevated nucleosome levels in systemic inflammation and sepsis. *Crit Care Med* 2003, 31(7):1947-1951.
17. Kirn T J, Weinstein M P: Update on blood cultures: how to obtain, process, report, and interpret. *Clin Microbiol Infect* 2013, 19(6):513-520.
18. Bryant J K, Strand C L: Reliability of blood cultures collected from intravascular catheter versus venipuncture. *Am J Clin Pathol* 1987, 88(1): 113-116.
19. Weinstein M P, Towns M L, Quartey S M, Mirrett S, Reimer L G, Parmigiani G, Reller L B: The clinical significance of positive blood cultures in the 1990s: a prospective comprehensive evaluation of the microbiology, epidemiology, and outcome of bacteremia and fungemia in adults. *Clin Infect Dis* 1997, 24(4):584-602.

The invention claimed is:

1. A method for determination of a pathogenic condition of a sample, comprising the following steps:
   a) providing a sample comprising at least one specific nucleic acid from a sample source, which nucleic acid is a free circulating DNA (cfDNA),
   b) providing a data base comprising at least one data set relating to the specific nucleic acid, which data set indicates the probability for the occurrence of at least one particular abundance of the specific nucleic acid in a control group,
   c) sequencing the at least one nucleic acid in the sample to determine the identity and abundance of the at least one specific nucleic acid in the sample,
   d) assigning the identity of the at least one specific nucleic acid determined in step c) to a data set of the data base provided in step b) which data set relates to the same specific nucleic acid determined in step c),
   e) computing a significance score indicating the pathogenic condition of the sample based on the abundance of the at least one specific nucleic acid of the sample determined according to step c) and the probability for the occurrence of the at least one particular abundance of the same specific nucleic acid in the control group provided in step b), wherein the significance score for a species j is calculated as $SIQ_j = C_j^* - (\log_{10}(P(X \geq C_j | \lambda_j)))$ wherein $P(X \geq C_j | \lambda_j)$ is the p-value to observe at least $C_j$ read counts, $\lambda_j$ is a species specific parameter and $C_j^*$ is the observed read count of the sample for species j.

2. The method according to claim 1, wherein the at least one data set relating to the specific nucleic acid refers to the specific nucleic acid or to a nucleic acid similar to the specific nucleic acid or to a nucleic acid derived from the same origin.

3. The method according to claim 1, wherein the sample source is an organism, preferably a human organism.

4. The method according to claim 1, wherein the sample is obtained from a sample source selected from the group consisting of whole blood, serum, blood plasma, liquor, urine, tissue, sputum, faeces or lavage, preferably from a cell-free fraction of the blood plasma.

5. The method according to claim 1, wherein the sample is blood plasma.

6. The method according to claim 1, wherein the sequencing is performed by molecular high-throughput sequence-analysis.

7. The method according to claim 1, wherein the pathogenic condition is characterized by the occurrence or by pathogenic quantities of nucleic acids of at least one viral, bacterial, fungal or parasitic organism.

8. The method according to claim 1, wherein the health condition is characterized by the occurrence or by above-threshold quantities of nucleic acids of at least one cancer cell.

9. The method according to claim 1, wherein the pathogenic condition is characterized by the occurrence or by above-threshold quantities of rejected cells of an implant.

10. The method according to claim 1, wherein the pathogenic condition is characterized by the occurrence or by pathogenic quantities of nucleic acids indicative for antibiotic resistance.

11. The method according to claim 1, wherein nucleic acids are not enriched prior to step c).

12. The method according to claim 1, wherein subsequent to step c) and prior to step d) a classification of nucleic acid sequences is performed.

13. The method according to claim 1, wherein the control group is characterized by a non-deviating condition, healthy condition or non-pathogenic condition.

14. The method according to 1, wherein a significance score indicating the deviation and/or pathogenic condition of the sample is computed based on the abundance of the at least one specific nucleic acid determined according to step c) and the probability for the occurrence of the at least one particular abundance of the same specific nucleic acid or the at least one second specific nucleic acid in the control sample provided in step b) by a central processing unit of the device.

\* \* \* \* \*

SEQUENCE LISTING

```
<160> NUMBER OF SEQ ID NOS: 4

<210> SEQ ID NO 1
<211> LENGTH: 240
<212> TYPE: DNA
<213> ORGANISM: Enterobacter cloacae

<400> SEQUENCE: 1
aataaattaa ccgaagataa aaaagaacct ctgctcaaca agttccagat tacaacttca      60
ccaggttcaa ctcaaaaaat attaacagca atgattgggt taaataacaa aacattagac     120
gataaaacaa gttataaaat cgatggtaaa ggttggcaaa aagataaatc ttggggtggt     180
tacaacgtta caagatatga agtggtaaat ggtaatatcg acttaaaaca agcaatagaa     240

<210> SEQ ID NO 2
<211> LENGTH: 150
<212> TYPE: DNA
<213> ORGANISM: Unknown
<220> FEATURE:
<223> OTHER INFORMATION: Sequence from Enterobacter cloacae isolated
      from human plasma
```

```
<400> SEQUENCE: 2
cagattacaa cttcaccagg ttcaactcaa aaaatattaa cagcaatgat tgggttaaat      60
aacaaaacat tagacgataa aacaagttat aaaatcgatg gtaaaggttg gcaaaaagat     120
aaatcttggg gtggttacaa cgttacaaga                                     150

<210> SEQ ID NO 3
<211> LENGTH: 150
<212> TYPE: DNA
<213> ORGANISM: Unknown
<220> FEATURE:
<223> OTHER INFORMATION: Sequence from Enterobacter cloacae isolated
      from human plasma

<400> SEQUENCE: 3
cagattacaa cttcaccagg ttcaactcaa aaaatattaa cagcaatgat tgggttaaat      60
aacaaaacat tagacgataa aacaagttat aaaatcgatg gtaaaggttg gcaaaaagat     120
aaatcttggg gtggttacaa cgttacaaga                                     150

<210> SEQ ID NO 4
<211> LENGTH: 147
<212> TYPE: DNA
<213> ORGANISM: Unknown
<220> FEATURE:
<223> OTHER INFORMATION: Sequence from Enterobacter cloacae isolated
      from human plasma

<400> SEQUENCE: 4
attacaactt caccaggttc aactcaaaaa atattaacag caatgattgg gttaaataac      60
aaaacattag acgataaaac aagttataaa atcgatggta aaggttggca aaagataaa     120 tcttggggtg gttacaacgt tacaaga                                        147
```